United States Patent

Perrone et al.

Patent Number: 4,886,793
Date of Patent: Dec. 12, 1989

[54] PENEM DERIVATIVES.

[75] Inventors: Ettore Perrone; Marco Alpegiani; Angelo Bedeschi, all of Milan; Franco Zarini, Settimo Milanese; Costantino Della Bruna, Rho; Giovanni Franceschi, Milan, all of Italy

[73] Assignee: Farmitalia Carlo Erba, S.r.l., Milan, Italy

[21] Appl. No.: 22,247

[22] Filed: Mar. 5, 1987

[30] Foreign Application Priority Data

Mar. 6, 1986 [GB] United Kingdom ................. 8605549

[51] Int. Cl.⁴ ................. C07D 499/00; A61K 31/425
[52] U.S. Cl. ................................... 514/192; 514/195; 540/310
[58] Field of Search ................. 540/310; 514/192, 193

[56] References Cited

U.S. PATENT DOCUMENTS

| | | | |
|---|---|---|---|
| 4,482,565 | 11/1984 | Foglio et al. | 424/270 |
| 4,558,042 | 12/1985 | Foglio et al. | 514/192 |
| 4,577,016 | 3/1986 | Albegiani et al. | 514/192 |
| 4,585,767 | 4/1986 | Cooke et al. | 514/210 |
| 4,623,643 | 11/1986 | Alpegiani et al. | 514/196 |
| 4,713,378 | 12/1987 | Perrone et al. | 514/192 |

FOREIGN PATENT DOCUMENTS 0236880 9/1987 European Pat. Off.
2187448 9/1987 United Kingdom.

OTHER PUBLICATIONS

Carey et al, Advanced Organic Chemistry, Part B, Reactions and Synthesis, Plenum 1977, pp. 407–414.

Primary Examiner—Nicholas S. Rizzo
Attorney, Agent, or Firm—Oblon, Spivak, McClelland, Maier & Neustadt

[57] ABSTRACT

There are provided compounds of formula I:

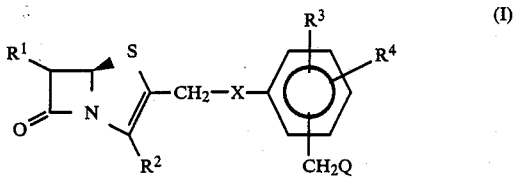

wherein
R$^1$ is hydrogen or a C$_1$–C$_4$ alkyl group either unsubstituted or substituted by one or more substituents chosen from a free or protected hydroxy or halogen atom;
R$^2$ is a free or esterified carboxy group or carboxylate anion;
R$^3$ and R$^4$ are each independently hydrogen or organic group,
X is —O—,

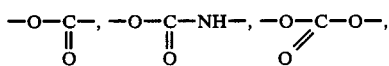

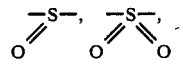

—S—,
Q is either
(a″) free or protected hydroxy, or
(b″) a C$_1$–C$_1$ acyloxy, or
(c″) carbamoyloxy OCONH$_2$, or
(d″) an optionally substituted heterocyclylthio group, or
(e″) an optionally substituted imido group, or
(f″) an optionally substituted quaternary ammonium group or
(g″) a halogen atom,
A and the pharmaceutically or veterinarily acceptable salts thereof. There are provided also methods for preparing compounds of formula I. The compounds of formula I are useful as antibacterial agents.

13 Claims, No Drawings

PENEM DERIVATIVES

The present invention relates to new penem compounds, to processes for their preparation, and to pharmaceutical and veterinary compositions containing them.

Compounds of the invention are penem derivatives of the following formula (I):

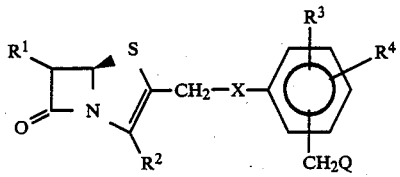

wherein
$R^1$ is hydrogen or a $C_1$–$C_4$ alkyl group either unsubstituted or substituted by one or more substituents chosen from a free or protected hydroxy or halogen atom;
$R^2$ is a free or esterified carboxy group or carboxylate anion;
$R^3$ and $R^4$ are each independently either hydrogen or
 (a) an optionally substituted $C_1$–$C_6$ alkyl, wherein two ortho alkyl groups may be linked to form a di- to decamethylene ring in which one ring C atom may be replaced by N, O, S, and which may contain one or two double bonds, or
 (b) an optionally substituted $C_2$–$C_6$ alkenyl, or
 (c) an optionally substituted $C_2$–$C_6$ alkynyl, or
 (d) an optionally substituted $C_1$–$C_6$ alkylsulphinyl or alkylsulphonyl, or
 (e) an optionally substituted $C_1$–$C_6$ alkanoyl, or
 (f) halogen, —$CF_3$, —CN, —CHO, or —$CONH_2$, or
 (g) OR, SR or NHR, wherein R represents hydrogen atom or an unsubstituted or substituted $C_1$–$C_6$ alkyl or $C_1$–$C_6$ alkanoyl group;
X is either
 (a') an oxygen atom, or
 (b') an oxycarbonyl group

or
 (c') an oxycarbonylamino group

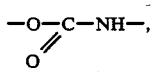

or
 (d') an oxycarbonyloxy (carbonate) group

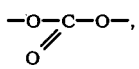

or
 (e') a sulphinyl group

or
 (f') a sulphonyl group

(g') a sulphur atom;
Q is either
 (a″) free or protected hydroxy, or
 (b″) a $C_1$–$C_4$ acyloxy, or
 (c″) carbamoyloxy $OCONH_2$, or
 (d″) an optionally substituted heterocyclylthio group, or
 (e″) an optionally substituted imido group, or
 (f″) an optionally substituted quaternary ammonium group or
 (g″) a halogen atom,
and the pharmaceutically or veterinarily acceptable salts thereof.

The present invention includes all the possible geometrical and optical isomers of the compounds of formula (I) either in the form of isomeric mixtures or in the form of the individual separated isomers. Preferably, the compounds of formula (I) have a (5R, 6S) configuration. The preferred $R^1$ group is an (α-hydroxy)ethyl radical and has a (1R) configuration, i.e. a R configuration at the α-carbon atom of the ethyl group.

As already said also the pharmaceutically or veterinarily acceptable salts of the compounds of formula (I) are included within the scope of the invention.

The said salts may be salts with inorganic bases such as, e.g., alkali or alkaline-earth metal hydroxides, in particular sodium and potassium hydroxides, and salts with organic bases such as, e.g., triethylamine, pyridine, benzylamine or collidine, including aminoacids such as, e.g., lysine or procaine. The invention includes also internal salts, i.e. zwitterions.

When $R^2$ is an esterified carboxy group it is a group COO— linked through the oxygen atom to an organic radical, such as a $C_1$–$C_6$ alkyl group, for instance methyl or ethyl; a halo-substituted $C_1$–$C_6$ alkyl group, for example 2,2,2-trichloroethyl; $C_2$–$C_6$ alkenyl group, for example allyl; an optionally substituted aryl group, for example phenyl and p-nitrophenyl; an optionally substituted aryl-$C_1$–$C_6$ alkyl group, for example benzyl, p-nitrobenzyl and p-methoxybenzyl; or groups such as benzhydryl, o-nitrobenzhydryl, acetonyl, trimethylsilyl, diphenyl-tert-butylsilyl, and dimethyl-tert-butylsilyl. The definition of $R^2$ as an esterified carboxy group includes also a carboxy group esterified with any residue, such as for instance acetoxymethyl, pivaloyloxymethyl or phthalidyl, which is known to be hydrolized "in vivo."

When Q is a protected hydroxy group, it is preferably protected with silyl groups, in particular trimethylsilyl, tert-butyldimethylsilyl, or with a carbonate, such as allyloxycarbonyl, p-nitrobenzyloxycarbonyl, or also with groups such as pyranyl, trifluoroacetyl, triphenylmethyl. When Q is an acyloxy group, it is preferably a $C_1$–$C_8$ alkanoyloxy, such as formyloxy, acetoxy, or a benzoyloxy group.

A heterocyclylthio group is a group

—S—Het wherein Het is a saturated or unsaturated, monocyclic or bicyclic ring, containing from 1 to 5 heteroatoms selected from oxygen, nitrogen and sulphur.

An imido group is a five or six-membered cyclic imido group

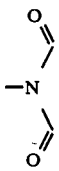

optionally incorporating, in addition to the imido nitrogen, one or two heteroatoms selected from nitrogen, oxygen and sulphur, said cyclic imido group being optionally fused with a benzene or pyridine ring.

A quaternary ammonium group is a group

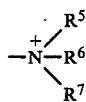

wherein
(1) $R^5$, $R^6$, $R^7$ are each independently an optionally substituted alkyl, aralkyl or aryl radical; or
(2) $R^5$ is as defined above under (1) and $R^6$, $R^7$ taken together with the nitrogen atom represent an optionally substituted heterocyclic radical, such radical being optionally fused with one phenyl ring or with a 5-7 membered, saturated or unsaturated cycloaliphatic or heterocyclic ring; or
(3) $R^5$, $R^6$, $R^7$, taken together with the nitrogen atom, represent an optionally substituted azoniabicyclo or azoniatricyclo radical; or
(4) $R^5$, $R^6$, $R^7$, taken together with the nitrogen atom, represent an optionally substituted pyridinium, pyrazolium, pirazinium, or pyridazinium radicals, such radicals being optionally fused with one phenyl ring or with 5-7 membered, saturated or unsaturated cycloaliphatic or heterocyclic ring.

Preferred substituents for the alkyl, alkenyl, alkynyl, cycloalkyl, alkylamino, alkoxy, alkylthio, alkylsulphinyl, alkylsulphonyl, alkanoyl groups under (a)–(g), the heterocyclylthio group under (d″) the imido group under (e″), and for the $R^5$, $R^6$, $R^7$ radicals of the ammonium group as defined above, are selected from the class consisting of (a‴) halogen, (b‴) hydroxy, (c‴) $C_1$-$C_4$ alkoxy, (d‴) $C_1$-$C_4$ alkylthio, (e) amino, optionally mono- or disubstituted with $C_1$-$C_4$ alkyl groups, (f‴) sulfo, (g‴) free or esterified carboxy, (h‴)-$CONH_2$ or CN, (k‴) carbamoyloxy, or hydroxycarbamoyl (l‴) hydroxyminomethyl (HO—N=CH—), α-methylhydroxyiminomethyl (HO—N=C($CH_3$)—) or methoxyiminomethyl ($CH_3$—O—N=CH—), (m‴) formamido or acetamido, (n‴) formyloxy or acetoxy, (o‴) $C_1$-$C_6$ alkanoyl group, (p‴) nitro, (q‴) $C_1$-$C_4$ alkyl group either unsubstituted or substituted by a substituent chosen from (a‴) to (p‴) above.

In the present specification, the term "halogen" preferably encompasses fluorine and chlorine atoms, but also iodine and bromine atoms. A $C_1$-$C_6$ alkyl group is, preferably, methyl or ethyl. In the definition of $R^3$/$R^4$, when such $R^3$, $R^4$ groups are linked together, they preferably form with the phenyl ring a bicyclic ring such as naphthyl, tetrahydronaphthyl, indanyl, indolyl, quinolyl.

A $C_2$-$C_6$ alkenyl group is, preferably, ethenyl or propenyl.

A $C_2$-$C_6$ alkynyl group is, preferably, ethynyl or propynyl.

A $C_1$-$C_4$ alkoxy group is, preferably, methoxy or ethoxy.

A $C_1$-$C_4$ alkylthio group is, preferably, methylthio or ethylthio.

A $C_1$-$C_6$ alkanoyl group is, preferably, formyl or acetyl.

A preferred class of compounds under this invention includes compounds of formula (I) wherein
$R^1$ is a 1-(hydroxy)ethyl group;
$R^2$ is sodium or potassium carboxylate COONa, COOK; or, when Q is a quaternary ammonium cation as defined above, $R^2$ is its carboxylate anion counterpart $COO^-$;
$R^3$ and $R^4$ are hydrogen, or each independently are hydrogen, hydroxy, formyloxy, acetoxy, carbamoyloxy; or $R^3$ and $R^4$ taken together are —CH=CH—CH=CH—;
X is as defined above;
Q is either hydroxy group or
(a‴″) acetoxy $OCOCH_3$, or
(b‴″) carbamoyloxy $OCONH_2$, or
(c‴″) a heterocyclylthio group selected from the following

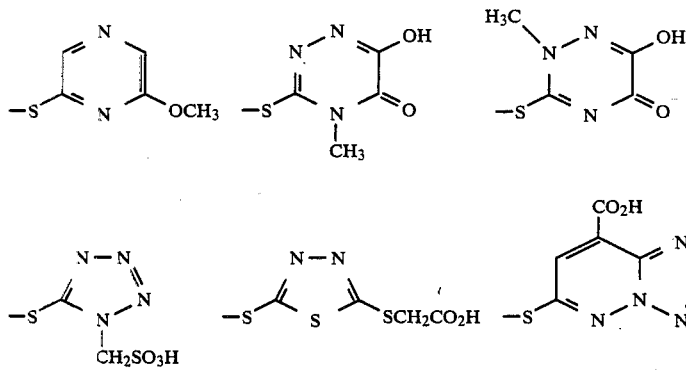

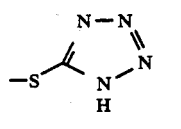 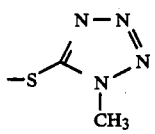 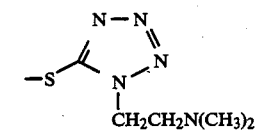

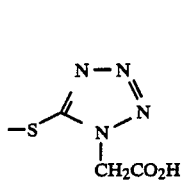 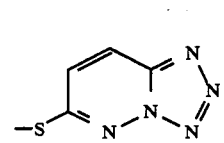

(d'''''') an imido group selected from the following

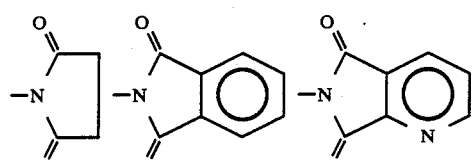

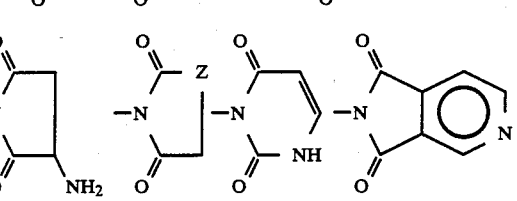

wherein Z represents NH, O or S, or
(e'''''') an ammonium group selected from the following

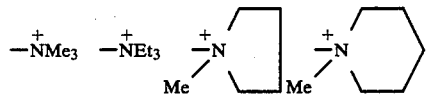

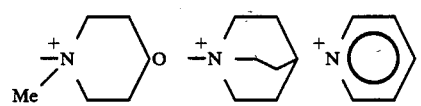

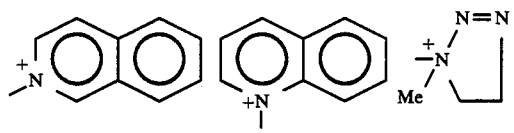

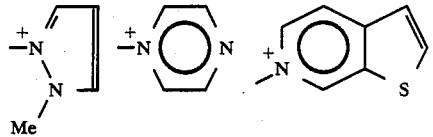

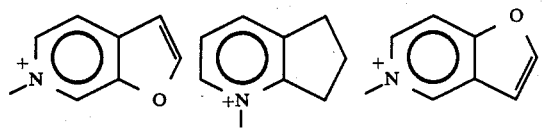

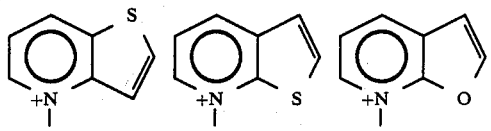

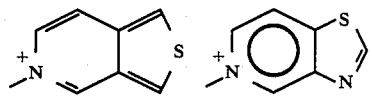

wherein the pyridinium, quinolinium, isoquinolinium, pyrazinium, thieno[2,3-c]pyridium, furo[2,3-c]pyridinium, furo[3,2-c]pyridinium, thieno[3,2-c]pyridinium, thieno[2,3-b]pyridinium, furo[2,3-b]pyridinium, thieno[3,4-c]pyridinium, and thiazolo[4,5-c]pyridinium rings are either unsubstituted or substituted by one or two substituents selected from those described under from (a''') to (p''') above.

Specific examples of preferred compounds of the invention are the acids listed in the following table, either as such or as the sodium, potassium or inner salt thereof.

TABLE I

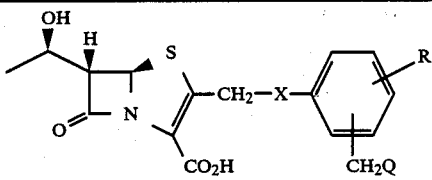

| Compound | —X— | —Q | R | orientation of substituents on the phenyl ring |
|---|---|---|---|---|
| 1 | —O— | —OCONH$_2$ | —H | para |

TABLE I-continued
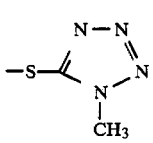
| Compound | —X— | —Q— | R | orientation of substituents on the phenyl ring |
|---|---|---|---|---|
| 2 | —O— | —OH | " | " |
| 3 | —O— | —OCOCH₃ | " | " |
| 4 | —O— | 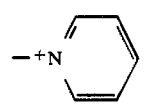 | " | " |
| 5 | —O— | 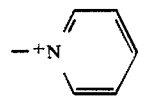 | " | " |
| 6 | —O— | 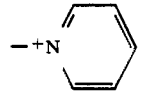 | " | meta |
| 7 | —O— | 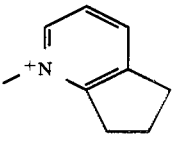 | " | ortho |
| 8 | —O— | 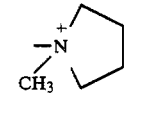 | " | para |
| 9 | —O— | 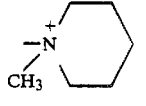 | " | " |
| 10 | —O— | 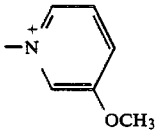 | " | " |
| 11 | —O— | 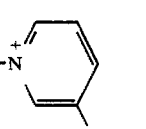 | " | " |
| 12 | —O— |  | " | " |

TABLE I-continued

Structure: β-lactam with (1-hydroxyethyl) group, S-CH=C(CO2H)-N, with substituent -CH2-X-phenyl(R)(CH2Q)

| Compound | -X- | -Q | R | orientation of substituents on the phenyl ring |
|---|---|---|---|---|
| 13 | -O- | -+N(CH3)(morpholine) | " | " |
| 14 | -O- | -+N(quinuclidine) | " | " |
| 15 | -O- | -N(succinimide) | " | " |
| 16 | -O- | -N(uracil) | " | " |
| 17 | -O- | -+N(pyridine) | -OH | (3)-OH, (4)-CH2Q |
| 18 | -OC(=O)- | -OCONH2 | -H | para |
| 19 | -OC(=O)- | -+N(pyridine) | " | " |
| 20 | -OC(=O)- | -+N(CH3)(pyrrolidine) | " | " |
| 21 | -OC(=O)- | -S-(1-methyltetrazol-5-yl) | " | " |
| 22 | -OCONH- | -OCONH2 | " | " |
| 23 | -OCONH- | -+N(pyridine) | " | " |

TABLE I-continued

[Structure: carbapenem core with (1-hydroxyethyl) substituent, methyl, S-CH2-X-phenyl(R)(CH2Q) side chain, CO2H on ring]

| Compound | —X— | —Q | R | orientation of substituents on the phenyl ring |
|---|---|---|---|---|
| 24 | —OCONH— | —⁺N(Me)(pyrrolidine) | " | " |
| 25 | —OCO— | —⁺N-pyridinium | " | " |
| 26 | —S— | —⁺N-pyridinium | " | " |
| 27 | —S(O)— | —⁺N-pyridinium | " | " |
| 28 | —S(O)— | —OCONH$_2$ | " | " |
| 29 | —S(O)$_2$— | —OCONH$_2$ | " | " |
| 30 | —S(O)$_2$— | —⁺N-pyridinium | " | " |
| 31 | O | —⁺N-(3,5-dimethylpyridinium) | " | " |
| 32 | O | —⁺N-(3-hydroxypyridinium) | " | " |
| 33 | O | —⁺N-pyridinium-CH$_2$CH$_2$SO$_3$H | " | " |
| 34 | O | —⁺N-pyridinium-CH$_2$OH | " | " |

TABLE I-continued
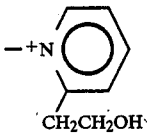
| Compound | —X— | —Q— | R | orientation of substituents on the phenyl ring |
|---|---|---|---|---|
| 35 | O | 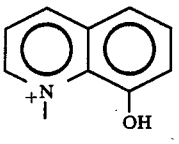 | " | " |
| 36 | O | 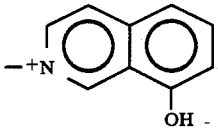 | " | " |
| 37 | O | 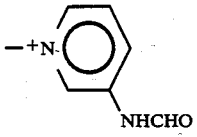 | " | " |
| 38 | O | 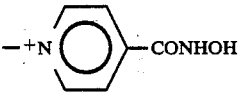 | " | " |
| 39 | O | 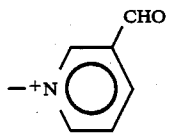 | " | " |
| 40 | O | 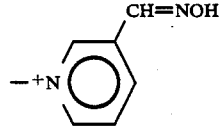 | " | " |
| 41 | O | 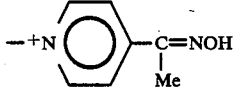 | " | " |
| 42 | O | 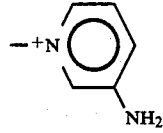 | " | " |
| 43 | O |  | " | " |

TABLE I-continued

[Structure: β-lactam with (1-hydroxyethyl) substituent, S, =CH-CH₂-X-phenyl-R with CH₂Q substituent, CO₂H]

| Compound | —X— | —Q— | R | orientation of substituents on the phenyl ring |
|---|---|---|---|---|
| 44 | O | [pyridazinium, N-attached] | " | " |
| 45 | O | [1-methyl-1,2,3-triazolium, N3-attached, Me on N1] | " | " |
| 46 | O | [1-methylpyrazolium, N2-attached] | " | " |
| 47 | O | [thieno[2,3-c]pyridinium, N-methyl] | " | " |
| 48 | O | [furo[2,3-c]pyridinium, N-methyl] | " | " |
| 49 | O | [furo[3,2-c]pyridinium, N-methyl] | " | " |
| 50 | O | [thieno[3,2-c]pyridinium, N-methyl] | " | " |
| 51 | O | [thieno[2,3-b]pyridinium, N-methyl] | " | " |
| 52 | O | [furo[2,3-b]pyridinium, N-methyl] | " | " |
| 53 | O | [thieno[3,4-c]pyridinium, N-methyl] | " | " |

TABLE I-continued

[Structure: (1-hydroxyethyl)-carbapenem core with CH₂-X-phenyl(R)(CH₂Q) substituent at C-2; CO₂H at C-3]

| Compound | —X— | —Q | R | orientation of substituents on the phenyl ring |
|---|---|---|---|---|
| 54 | O | 1-methylpyrido[thiazolo]-N⁺ (thiazolopyridinium) | " | " |
| 54/A | O | +N-pyridinium-CH₂SO₃Na | " | " |
| 55 | O | +N-pyridinium-SO₃Na (3-) | " | " |
| 56 | O | +N-pyridinium-SO₃Na (2-) | " | " |
| 57 | O | +N-pyridinium-CO₂H (4-) | " | " |
| 58 | O | +N-pyridinium-CO₂H (3-) | " | " |
| 59 | O | +N-pyridinium-CH₂CO₂H (4-) | " | " |
| 60 | O | +N-pyridinium-CH₂CO₂H (3-) | " | " |
| 61 | O | +N-pyridinium-CONH₂, CO₂H | " | " |

TABLE I-continued

[Structure: β-lactam core with (OH)(H)-CH(CH₃) group, S-CH₂-X-phenyl(R)(CH₂Q), CO₂H on N-containing ring]

| Compound | —X— | —Q | R | orientation of substituents on the phenyl ring |
|---|---|---|---|---|
| 62 | O | 2-Cl-3-CO₂H-pyridinium (+N) | " | " |
| 63 | O | pyridinium-SCH₂CO₂H | " | " |
| 64 | O | pyridinium-SCH₂CO₂H | " | " |
| 65 | O | N-methylpiperidinium-CO₂H | " | " |
| 66 | O | N-methylpiperidinium-CO₂H | " | " |
| 67 | O | N-methylpyrrolidinium-CO₂H | " | " |
| 68 | O | N-methylpyrrolidinium-CO₂H | " | " |
| 69 | O | +N(CH₃)₂—CH₂CO₂H | " | " |
| 70 | O | 4-N(CH₃)₂-pyridinium | " | " |

TABLE I-continued

[Structure: carbapenem core with OH, H, CH₃ stereochemistry, S-CH₂-X-phenyl(R)(CH₂Q), CO₂H]

| Compound | —X— | —Q | R | orientation of substituents on the phenyl ring |
|---|---|---|---|---|
| 71 | O | 2-(dimethylamino)pyridinium (+N, N(CH₃)₂) | " | " |
| 72 | O | 4-(pyrrolidin-1-yl)pyridinium | " | " |
| 73 | O | 4-(pyridin-2-yl)pyridinium | " | " |
| 74 | O | 4-(aminomethyl)pyridinium | " | " |
| 75 | O | 3-(aminomethyl)pyridinium | " | " |
| 76 | O | 2-(aminomethyl)pyridinium | " | " |
| 77 | O | 3-(pyrrolidin-1-ylmethyl)pyridinium | " | " |
| 78 | O | 1-methyl-4-(piperazin-1-yl) (+N-CH₃, NH) | " | " |
| 79 | O | 1,1-dimethyl-4-methylpiperazinium | " | " |

The compounds of formula (I) may be prepared, according to the processes of the present invention, either by cyclizing a compound of formula (II),

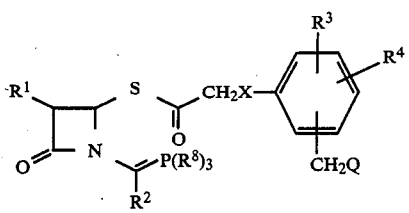

wherein $R^1$, $R^2$, $R^3$, $R^4$, X and Q are as defined above, and $R^8$ is either lower alkoxy, preferably methoxy or ethoxy, or aryl, preferably phenyl, or by reacting a compound of formula (III), or protected derivative thereof,

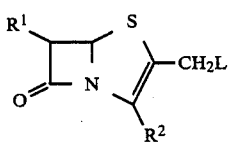

wherein $R^1$ and $R^2$ are as defined above and L is hydroxy group or a chlorine atom, with a compound of formula (IV), or a salt thereof,

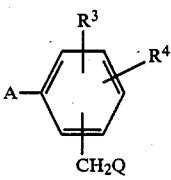

wherein $R^3$, $R^4$ and Q are as above defined and A represents

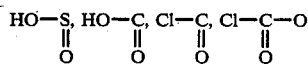

or O=C=N.

A resultant compound of formula (I) wherein Q represents hydroxy group or a halogen atom may be converted into another compound of formula I wherein Q is different by reaction with a suitable reagent, according to the individual meaning of the group Q encompassed by the present invention, i.e. with a reagent known in the art to be able to convert a benzylic alcohol or halide into a compound Ph—CH$_2$—Q, wherein Q is as defined above.

A compound of formula (I) wherein X is sulphur atom may be converted into another compound of formula (I) wherein X is sulphinyl by reaction with an organic or inorganic oxidizing agent suitable for the conversion of a sulphide into a sulphoxide, such as, for example, m-chloroperoxybenzoic acid, peracetic acid, perphthalic acid, sodium periodate, osmium tetraoxide or hydrogen peroxide.

Lastly, the optionally present protecting groups are removed, and/or an obtained compound of formula (I) is converted into a salt thereof, and/or a resultant mixture of isomers is separated into the single components.

The cyclization of a compound of formula (II) into a compound of formula (I), or a protected derivative thereof, is carried out by heating the former in an inert solvent, such as toluene or xylene, preferably under nitrogen or argon, at temperatures ranging from approx. +40° C. to +140°C.

The reaction of a compound of formula (III) with a compound of formula (IV) to afford a compound of formula (I) may be carried out under known-per-se procedures, i.e. under conditions known to convert an allyl alcohol or an activated derivative thereof or an allyl chloride into (a) an allyl phenyl ether, or (b) an allyl benzoate, or (c) an O-allyl N-phenyl carbamate, or (d) an allyl phenyl carbonate, or (e) an allyl phenyl sulphoxide, or (f) an allyl phenyl sulphone, or (g) an allyl phenyl sulphide, according to whether the X group in the compound of formula (I) is (a) an oxygen atom, or (b) an oxycarbonyl group, or (c) an oxycarbonylamino group, or (d) an oxycarbonyloxy group, or (e) a sulphinyl group, or (f) a sulphonyl group, or (g) a sulphur atom.

General procedures for the conversion of a compound of formula (I) wherein Q is hydroxy, or a protected derivative thereof, into a compound of formula (I) wherein Q, being as defined by the present invention, is different from hydroxy, or into a protected dertivative thereof, are as detailed below:

(1) a compound of formula (I) wherein Q is acyloxy may be obtained by reaction with the suitable acyl chloride or anhydride, preferably in the presence of a base, or with the suitable carboxylic acid under Mitsunobu conditions, i.e. in the presence of a phosphine, e.g. triphenylphosphine, and an azodicarboxylate, e.g. diethyl azodicarboxylate (see, for example, *Synthesis* 1981, 1);

(2) a compound of formula (I) wherein Q is carbamoyloxy may be obtained by reaction with an isocyanate, such as trichloroacetyl isocyanate or chlorosulphonyl isocyanate, followed by conventional removal of the trichloroacetyl or chlorosulphonyl groups;

(3) a compound of formula (I) wherein Q is an optionally substituted heterocyclylthio group may be obtained by reaction with the heterocyclyl thiol to which the desired group Q corresponds, or with a salt thereof with an organic or inorganic base; said reaction being carried out either under Mitsunobu conditions, or by first activating the hydroxy group of the starting compound of formula (I) wherein Q is hydroxy into a leaving group, such as a mesylate or a tosylate;

(4) a compound of formula (I) wherein Q is an imido group may be obtained by reaction with the imide to which the desired group Q corresponds, said reaction being preferably carried out under Mitsunobu conditions;

(5) a compound of formula (I) wherein Q is a quaternary ammonium group may be obtained from a compound of formula (I) wherein Q is hydroxy by converting such hydroxy group into a leaving group, preferably a triflate, which is then displaced, preferably in situ, by the parent amine to which the desired group Q corresponds.

As already said, compounds of formula (I) can be prepared from compounds of formula (I) wherein Q represents halo, by reaction with the appropriate nucleophile to which the desired group Q corresponds, e.g. a $C_1$–$C_4$ carboxylate, the salt of an heterocyclic thiol or of an imide, or a tertiary or aromatic amine. The general conditions of such reactions, as well of the reactions listed above under (1)–(5), are those known in the art for the conversion of a benzyl halide or benzyl alcohol into a compound of formula Ph—CH$_2$—Q, wherein Q is as defined above.

Intermediates of formula (II) are known or can be prepared starting from known compounds according to known methodologies, for example according to the methods described in *J.Am.Chem.Soc.* 1978, 100, 8214 or *Chem.Pharm.Bull.* 1983, 31, 768. Penem intermediates of formula (III) and reagents of formula (IV) are either known compounds or may be obtained from known compounds according to known-per-se procedures.

The compounds of formula (I) provided by the present invention are broad-spectrum, potent antibacterial agents, or are useful intermediates thereof.

When tested in vivo, they showed a particularly interesting pharmacokinetic profile, and a high degree of therapeutic effectiveness in treating infections caused by Gram-positive and -negative bacteria. Moreover, especially in the form of enzymatically labile esters, such as the acetoxymethyl esters, the compounds of formula (I) were found effective when administered orally. Included within the invention are therefore pharmaceutical or veterinary compositions containing the compounds of formula (I) and conventional carriers or diluents.

The compounds of the formula I according to the invention are effective in vitro in the folllowing dosage ranges: against cocci (inclusive of penicillinase-formers), from 0.001 to 1 mcg/ml; agaist entero bacteria (inclusive of β-lactamase-formers), from 0.5 to 50 mcg/ml:

In vivo data for (5R,6S)-6-[(1R)-hydroxy ethyl]-2-[4-(1-pyridinio)methylphenyl]oxymethylpenem-3-carboxylate (example 1, Compound 5,FCE 24386)

| Pharmacokinetios parameters | A.U.C. (mcg/ml min.) | t ½β | % Absorption s.c. |
|---|---|---|---|
| Mouse | 3361 | 27' | 100 |
| Rat | 6150 | 28' | — |

| Experimental infections in mice[1] | |
|---|---|
| Strain | ED$_{50}$(mg/kg, cumulative dose) |
| Staphilococcus aureus Smith | <<0.032 |
| Escherichia coli G II | 1.55 |

[1]Intraperitoneal infection in mice with a 3 × LD$_{50}$ challenge; treatments at 30, 90 and 360 minutes after infection.

When tested in vivo after parenteral administration, the compounds of formula I of the present invention showed a very high degree of therapeutic effectiveness in treating infections caused by both Gram-positive and Gram-negative bacteria, their toxicity being on the other hand quite negligible.

Owing to their high antibacterial activity the compounds of the invention are thus useful, for example, in the treatment of respiratory tract infections, for example, bronchitis, bronchopneumonia, pleurisy; hepatobiliary and abdominal infections, for example, septicemia; urinary tract infections, for example, pyelonephritis, cystitis; obstetrical and gynecological infections, for instance, cervicitis, endometritis; ear, nose and throat infections, for instance otitis, sinusitis, parotitis.

The compounds of the invention may be administered, either to humans or to animals, in a variety of dosage forms, e.g., orally in the form of tablets, capsules, drops or syrups; rectally in the form of suppositories; parenterally, e.g., intravenously or intramuscularly (as solutions or suspensions), with intravenous administration being preferred in emergency situation; by inhalation in the form of areosols or solutions for nebulizers; intravaginally in the form, e.g., of pessaries; or topically in the form of lotions, creams and ointments. The pharmaceutical or veterinary compositions containing the compounds of formula (I), which are too within the scope of the invention, may be prepared in a conventional way by employing the conventional carriers or diluents used for, e.g., cephalosporins.

Conventional carriers or diluents are, for example, water, gelatine, lactose, starches, magnesium stearate, talc, vegetable oils, cellulose and the like. Daily doses in the range of about 0.5 to about 100 mg per kg of body weight may be used, in various animal species, the exact dose depending on the age, weight and condition of the subject to be treated and on the frequency and route of administration.

A preferred way of administration of the compounds of the invention is the parenteral one: in this case the compounds may be administered, for example to adult humans, in an amount ranging from about 200 mg to about 800 mg pro dose, preferably about 400 mg pro dose, 1–4 times a day, dissolved in a suitable solvent, such as, for example, sterile water or lidocaine hydrochloride solution for intramuscular injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with, suspended or dissolved in conventional inert dry or aqueous carriers for application by washing or spraying.

They are also useful as nutritional supplements in animal feeds.

The following examples illustrate but do not limit the present invention.

EXAMPLE 1

(5R,6S)-6-[(1R)-hydroxyethyl]-2-[4-(1-pyridinio)methylphenyl]oxymethylpenem-3-carboxylate (Compound 5)

Step A

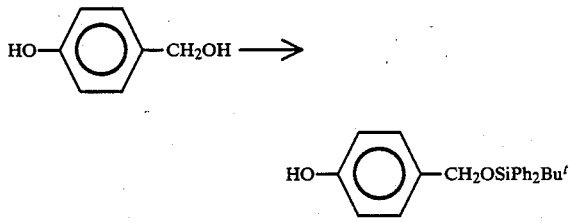

A stirred solution of 4-hydroxymethylphenol (6,2 g) in dry dimethylformamide (100 ml) was treated sequentially with imidazole (9,5 g) and tert-butyldiphenylsilyl chloride (12.8 ml) at room temperature.

The resulting solution was stirred 2 hours at room temperature, then poured into diisopropyl ether and washed twice with water. The organic layer was dried over Na$_2$SO$_4$ and the solvent removed in vacuo.

Purification through a silica gel column (230–400 Mesh, n-hexane/ethyl acetate mixtures as eluant) yielded 4-tert-butyldiphenylsilyloxymethylphenol as an oil (12.0 g); NMR (60 MHz, CDCl3)δ ppm: 1.13 (9H, s), 4.72 (2H, s), 5.53 (1H, br s, exch. D2O), 6.73 (2H, d, J=9.0 Hz), 7.17 (2H, d, J=9.0 Hz), 7.3-7.7 (10H, m)

Step B

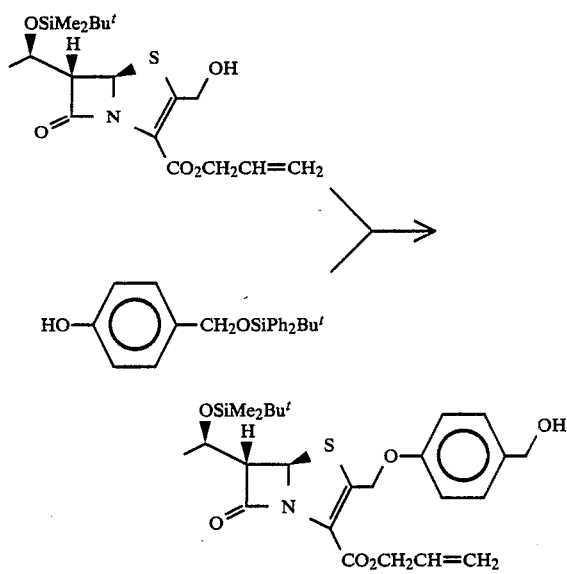

A solution of diethylazodicarboxylate (4 mM) and triphenylphosphine (4 mM) in tetrahydrofuran (10 ml) was stirred at 0° C. for 1 hour. This mixture was added to a solution of allyl (5R,6S)-6-[(1R)-tert-butyldimethylsilyloxyethyl]-2-hydroxymethylpenem-3-carboxylate (1.0 g) and 4-tert-butyldiphenylsilyloxymethylphenol (1.0 g) in dry tetrahydrofuran (20 ml) at 0° C. The resulting solution was stirred 30 minutes at room temperature, then concentrated in vacuo and purified by flash chromatography on silica gel to give allyl (5R,6S)-6-[(1R)-tert-butyldimethylsilyloxyethyl]-2-(4-tert-butyldiphenylsilyloxymethylphenyl)oxymethylpenem-3-carboxylate as a pale yellow syrup (600 mg).

A solution of this product in tetrahydrofuran (20 ml) was stirred for 8 hours at room temperature in the presence of acetic acid (0.40 ml) and tetrabutylammonium fluoride trihydrate (0.40 g). The solvent was removed in vacuo and the residue fractionated through a silica gel column (Merck 60 HR 230-400 Mesh; n-hexane/ethyl acetate mixtures as eluant) to give allyl (5R,6S)-6-[(1R)-tert-butyldimethylsilyloxyethyl]-2-(4-hydroxymethylphenyl)oxymethylpenem-3-carboxylate (370 mg); IR (CHCl3) $\nu_{max}$ 1787, 1702, 1605, 1580 cm$^{-1}$; NMR (200 MHz, CDCl3)δ ppm: 0.06 (6H, s), 0.86 (9H, s), 1.21 (3H, d, J=6.4 Hz), 3.70 (1H, dd, J=1.7 and 4.6 Hz), 4.22 (1H, dq, J=4.6 and 6.4 Hz), 4.62 (2H, s), 4.70 (2H, m), 5.26 (1H, d, J=10.3 Hz), 5.13 and 5.39 (2H, ABq, J=15.6 Hz), 5.41 (1H, d, J=17 Hz), 5.58 (1H, d, J=1.7 Hz), 5.91 (1H, m), 6.91 and 7.29 (each 2H, d, J=8.7 Hz).

Step C

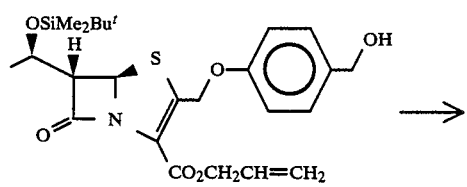

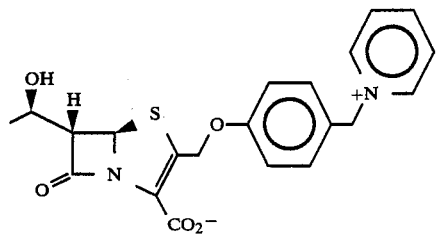

A solution of allyl (5R, 6S)-6-[(1R)-tert-butyldimethylsilyloxymethyl]-2-(4-hydroxymethylphenyl)oxymethylpenem-3-carboxylate (200 mg) in dry, ethanol-free dichloromethane (15 ml) was cooled under nitrogen to −70° C. and then sequentially treated under stirring with pyridine (0.23 ml) and trifluoromethanesulphonic anhydride (0.22 ml). The reaction mixture was let rise to −5° C. and then quenched with 0.1M aqueous HCl. The organic layer was separated, washed with brine, dried and evaporated to give a gummy residue.

This product was taken up in tetrahydrofuran (8 ml) and treated in sequence with acetic acid (0.55 ml) and tetrabutylammonium fluoride. 3 H2O (0.5 g). The clear solution was let stand for 20 hours at room temperature, then concentrated and passed through a silica gel column (230-400 Mesh, φ2 cm, h 8 cm). Elution with neat CH2Cl2, CH2Cl2/CH3CN (70:30 and then 50:50) and neat acetonitrile was followed by a final washing with CH3CN/H2O (1:2). Addition of NaCl to the last fractions and extraction with CH3CN, followed by concentration in vacuo, gave the crude allyl ester of the title product as a foam.

This material in 5 ml of CH2Cl2 and 0.1 ml of acetic acid was stirred with triphenylphosphine (0.025 g) and tetrakis (triphenylphosphine) Pd (0) (0.025 g) for 30 min., after which time an additional amount of PPh3 (0.02 g) and Pd(PPh3)4 (0.02 g) was added to complete the reaction (further 15 min.).

The reaction mixture was concentrated and the residue triturated with ethyl acetate. The obtained solid was dissolved in demineralized water and chromatographed on LiChroprep RP-18 eluting first with water and then with 10% CH3CN in H2O.

The appropriate fractions were combined and freeze-dried to afford 30 mg of the title compound as a white powder; UV (H2O) $\lambda_{max}$ 258 and 307 nm; IR (KBr) $\nu_{max}$ 1765, 1600 cm$^{-1}$; NMR (200 MHz, D2O)δ ppm: 1.22 (3H, d, J=6.3 Hz), 3.72 (1H, dd, J=1.5 and 6.0 Hz), 4.14 (1H, dq, J=6.0 and 6.3 Hz), 5.02 and 5.34 (2H, each d, J=14.4 Hz), 5.43 (1H, d, J=1.5 Hz), 5.70 (2H, s), 6.95, 7.39 (2H, each d, J=8.6 Hz), 8.01 (2H, dd, J=5.6, 7.0 Hz), 8.50 (1H, t, J=7.0 Hz), 8.87 (2H, d, J=5.6 Hz).

EXAMPLE 2

By following the experimental procedure described in the above Example 1 and replacing pyridine with 2,3-cyclopentenopyridine, N-methylpyrrolidine, N-methylpiperidine, 3-methoxypyridine, 3-cyanomethylpyridine, N-methylmorpholine, quinuclidine, there were obtained, respectively:

(5R,6S)-6-[(1R)-hydroxyethyl]-2-[4-(2,3-cyclopenteno-1-pyridinio)methylphenyl]oxymethylpenem-3-carboxylate (Compound 8);

(5R,6S)-6-[(1R)-hydroxyethyl]-2-[4-(1-methyl-1-pyrrolidinio)methylphenyl]oxymethylpenem-3-carboxylate (Compound 9);

NMR (200 MHz, D$_2$O)δ ppm: 1.27 (3H, d, J=6.3 Hz), 2.22 (4H, m), 2.93 (3H, s), 3.30–3.65 (4H, m), 3.84 (1H, d, J=6.0 Hz), 4.23 (1H, m), 4.45 (2H, s), 5.19 and 5.51 (2H, two d, J=14 Hz), 5.58 (1H, s), 6.95–7.55 (4H, m).

UV (H$_2$O) λ$_{max}$ 308 nm.

IR (KBr) γ$_{max}$ 1760, 1605, 1580 nm.

(5R,6S)-6-[(1R)-hydroxyethyl]-2-[4-(1-methyl-1-piperidinio)methylphenyl]oxymethylpenem-3-carboxylate (Compound 10);

(5R,6S)-6-[(1R)-hydroxyethyl]-2-[4-(3-methoxy-1-pyridinio)methylphenyl]oxymethylpenem-3-carboxylate (Compound 11);

(5R,6S)-6-[(1R)-hydroxyethyl]-2-[4-(3-cyanomethyl-1-pyridinio)methylphenyl]oxymethylpenem-3-carboxylate (Compound 12);

(5R,6S)-6-[(1R)-hydroxyethyl]-2-[4-(4-methyl-4-morpholinio)methylphenyl]oxymethylpenem-3-carboxylate (Compound 13);

(5R,6S)-6-[(1R)-hydroxyethyl]-2-[4-(1-quinuclidinio)-methylphenyl]oxymethylpenem-3-carboxylate (Compound 14).

EXAMPLE 3

(5R,6S)-6-[(1R)-hydroxyethyl]-2-[4-(1-pyridinio)methylphenyl]oxymethylpenem-3-carboxylate (Compound 5)

Step A

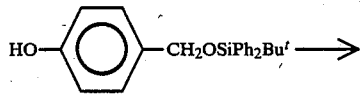

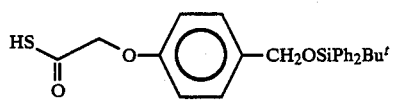

A solution of 4-tert-butyldiphenylsilyloxymethylphenol (see Example 1, Step A) (13 g) and ethyl bromoacetate (4.0 ml) in acetone (50 ml) was refluxed for 40 h in the presence of sodium iodide (5.37 g) and potassium carbonate (4.69 g). The reaction mixture was partitioned between ethyl ether and water, and the dried (MgSO$_4$) organic phase was evaporated. Silica gel chromatography of the residue afforded ethyl 2-(4-tert-butyldiphenylsilyloxymethylphenyl)oxyacetate as a colourless syrup (8 g); IR ν$_{max}$ 1735 cm$^{-1}$; NMR (60 MHz, CDCl$_3$)δ 1.1 (9H, s), 1.3 (3H, t, J=6 Hz), 4.2 (2H, q, J=6 Hz), 4.55 and 4.65 (each 2H, s), 6.8–7.8 (10H, m).

A solution of this material (7.7 g) in tetrahydrofuran (120 ml) was stirred for 30' with 10% aq. KOH (25 ml). The reaction mixture was made acidic with 10% H$_2$SO$_4$ and extracted with dichloromethane. The organic layer was washed with aq. NaCl, dried (MgSO$_4$) and evaporated to obtain 2-(4-tert-butyldiphenylsilyloxymethylphenyl)oxyacetic acid (7.2 g) as a yellowish oil;

IR (film) ν$_{max}$ 3500–2500, 1725 cm$^{-1}$; NMR (60 MHz, CDCl$_3$)δ1.10 (9H, s), 4.55 and 4.60 (each 2H, s), 6.8–7.8 (10H, m), 8.2 br (1H, s).

A solution of the above product (7.0 g) in dry, ethanol-free dichloromethane (120 ml) was treated at −40° C. with triethylamine (2.5 ml) and ethyl chlorocarbonate (1.72 ml). After 20 minutes at the same temperature, a second amount of NEt$_3$ (2.5 ml) was added, and hydrogen sulfide was bubbled under stirring for 40 minutes at −20° C. The reaction mixture was let rise to room temperature and then washed with 4% aq. HCl, dried and evaporated to afford 2-(4-tert-butyldiphenylsilyloxymethylphenyl)oxyacetic S-acid (7.2 g) as a yellowish oil; IR (CHCl$_3$) ν$_{max}$ 2560, 1690 cm$^{-1}$; NMR (60 MHz, CDCl$_3$)δ 1.1 (9H, s), 4.2 (1H, br s), 4.4 and 4.6 (each 2H, s), 6.7–7.7 (10H, m).

Step B

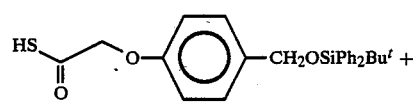

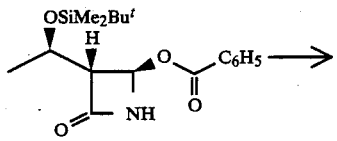

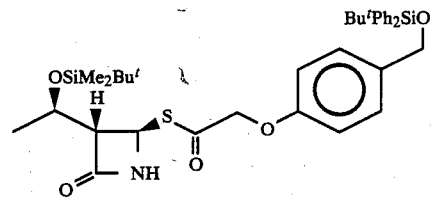

A solution of 2-(4-tert-butyldiphenylsilyloxymethylphenyl)oxyacetic S-acid (8.7 g) in acetone (50 ml) was sequentially treated at 10° C. under stirring with 1N aq. NaOH (20 ml) and (3R)-[(1R)-tert-butyldimethylsilyloxyethyl]-(4R)-benzoyloxyazetidin-2-one (7 g). More 1N NaOH was added, as needed, to keep the pH at about 8.0 while stirring at 10° C. for 15 minutes, after which time the reaction mixture was partitioned between isopropyl ether and water. The organic phase was dried, evaporated and purified by flash-chromatography, thereby obtaining (3S)-[(1R)-tert-butyldimethylsilyloxyethyl]-(4R)-(4-tert-butyldiphenylsilyloxymethylphenyl)oxyacetylthioazetidin-2-one (4.5 g); IR (CHCl$_3$) ν$_{max}$ 1760, 1680 cm$^{-1}$; NMR (60 MHz, CDCl$_3$)δ 0.05 (6H, s), 0.85 and 1.05 (each 9H, s), 1.15 (3H, d, J=6.5 Hz), 3.15 (1H, dd, J=2.5 and 4 Hz), 4.2 (1H, m), 4.6 (2H, s), 5.25 (1H, d, J=2.5 Hz), 6.3 (1H, br s), 7.75–8.7 (10H, m).

Step C

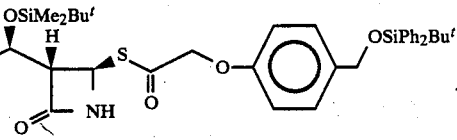

-continued

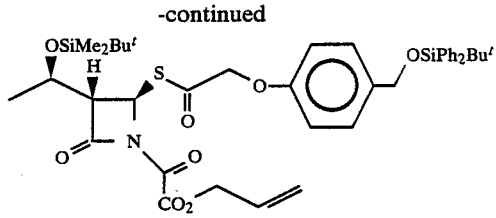

A solution of (3S)-[(1R)-tert-butyldimethylsilyloxyethyl]-(4R)-(4-tert-butyldiphenylsilyloxymethylphenyl)oxyacetylthioazetidin-2-one (2.5 g) and allyloxyoxalyl chloride (0.67 g) in dichloromethane was treated at 5° C. with triethylamine (0.63 ml). After 45 min, the reaction mixture was washed with water, dried (MgSO$_4$) and evaporated, thereby obtaining crude 1-allyloxyoxalyl-(3S)-[(1R)-tert-butyldimethylsilyloxyethyl]-(4R)-(4-tert-butyldiphenylsilyloxymethylphenyl)oxyacetylthioazetidin-2-one (2.7 g); IR (CHCl$_3$) $\nu_{max}$ 1810, 1755, 1710 cm$^{-1}$; NMR (60 MHz, CDCl$_3$)δ ppm: 0.03 (6H, s), 0.85 and 1.1 (each 9H, s), 1.2 (3H, d, J=6.5 Hz), 3.4 (1H, dd), 4.3 (1H, m), 4.6–4.8 (6H, m), 5.2–5.5 (2H, m), 5.6–5.8 (1H, m), 6.02 (1H, d, J=3.5 Hz), 6.8–7.7 (10H, m).

Step D

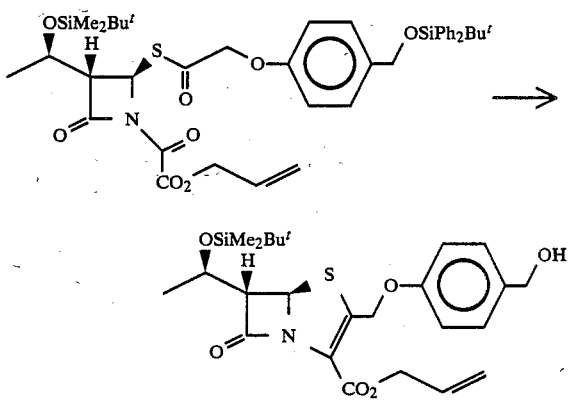

The 1-allyloxyoxalylazetidin-2-one obtained in Step C above (2.7 g) was refluxed in toluene for 5 hours in the presence of triethyl phosphite (1.31 ml). The solvent was removed in vacuo and the crude product purified by silica gel chromatography, thereby obtaining allyl (5R,6S)-6-[(1R)-tert-butyldimethylsilyloxyethyl]-2-(4-tert-butyldiphenylsilyloxymethylphenyl)oxymethylpenem-3-carboxylate (1.4 g). Selective desilylation of this material, as described in Example 1, Step B, afforded allyl (5R,6S)-6-[(1R)-tert-butyldimethylsilyloxyethyl]-2-(4-hydroxymethylphenoxy)methylpenem-3-carboxylate.

Step E

From the above material, the title product was obtained as described in Example 1, Step C.

EXAMPLE 4

By following the experimental procedure described in the Example 3 above, but starting from 3-tert-butyldiphenylsilyloxymethylphenol, there was obtained:

(5R,6S)-6-[(1R)-hydroxyethyl]-2-[3-(1-pyridinio)methylphenoxy]methylpenem-3-carboxylate (Compound 6).

EXAMPLE 5

(5R,6S)-6-[(1R)-hydroxyethyl]-2-[4-(1-pyridinio)methylphenoxy]methylpenem-3-carboxylate (Compound 5).

Step A

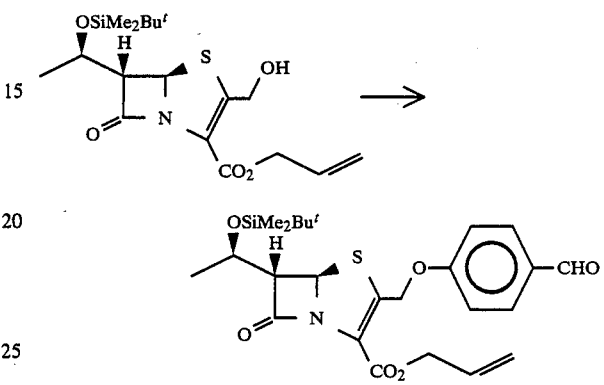

Diethyl azodicarboxylate (0.992 ml) was dropped under stirring into a cold (0° C.) solution of allyl (5R,6S)-6-[(1R)-tert-butyldimethylsilyloxyethyl]-2-hydroxymethylpenem-3-carboxylate (2.3 g), p-hydroxybenzaldehyde (702 mg) and triphenylphosphine (1.66 g) in dry THF (70 ml). The reaction mixture was let rise to room temperature while monitoring the depletion of the reagents by TLC. The solvent was removed in vacuo and the residue purified by flash-chromatography (SiO$_2$, cyclohexane-ethyl acetate from 9:1 to 1:2), thereby obtaining allyl (5R,6S)-6-[(1R)-tert-butyldimethylsilyloxyethyl]-2-(4-formylphenoxy)methylpenem-3-carboxylate (2.85 g) as a yellowish syrup; IR (CHCl$_3$) $\nu_{max}$ 1790, 1695 br, 1600 cm$^{-1}$; NMR (CDCl$_3$, 200 MHz)δ ppm: 0.05 (6H, s), 0.86 (9H, s), 1.21 (3H, d, J=6.3), 3.70 (1H, dd, J=1.6 and 4.4 Hz), 4.23 (1H, dq, J=4.4 and 6.3 Hz), 4.69 (2H, m), 5.21 and 5.50 (each 1H, d, J=15.1 Hz), 5.26 (1H, d, J=10 Hz), 5.40 (1H, d, J=18 Hz), 5.61 (1H, d, J=1.6 Hz), 5.92 (1H, m), 7.03 and 7.85 (each 2H, d, J=8.9 Hz), 9.90 (1H, s).

Step B

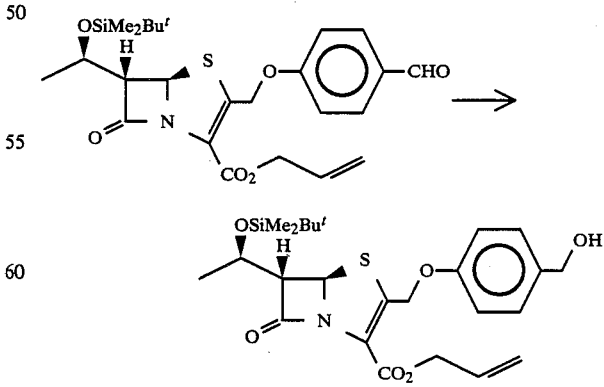

Acetic acid (1 ml) and sodium cyanoborohydride (1.2 g) were sequentially added to a solution of allyl (5R,6S)-6-[(1R)-tert-butyldimethylsilyloxyethyl]-2-(4-formylphenoxy)methylpenem-3-carboxylate (2.15 g) in dry tetrahydrofuran (55 ml). After 30 minutes more hydride (1.2 g) was added. The mixture was stirred for additional 20 minutes, then partitioned between water and ethyl acetate. Removal of the solvent from the dried (MgSO$_4$) organic layer, followed by flash-chromatography on silica, afforded allyl (5R,6S)-6-[(1R)-tert-butyldimethylsilyloxyethyl]-2-(4-hydroxymethylphenoxy)-methylpenem-3-carboxylate (2.0 g), identical with the material described in Example 1, Step B.

Step C

From the above material, the title product was obtained as described in Example 1, Step C.

EXAMPLE 6

By following the experimental procedure described in the Example 5 above, but substituting salicylaldehyde for 4-hydroxybenzaldehyde, there was obtained:

(5R,6S)-6-[(1R)-hydroxyethyl]-2-[2-(1-pyridinio)methylphenoxy]methylpenem-3-carboxylate (Compound 7).

EXAMPLE 7

Similarly, following the experimental procedure described in Example 5, but substituting 2,4-dihydroxybenzaldehyde for 4-hydroxybenzaldehyde, there was obtained:

(5R,6S)-6-[(1R)-hydroxyethyl]-2-[2-hydroxy-4-(1-piridinio)methylphenoxy]methylpenem-3-carboxylate (Compound 17).

EXAMPLE 8

Sodium (5R,6S)-6-[(1R)-hydroxyethyl]-2-(4-hydroxymethylphenoxy)methylpenem-3-carboxylate (Compound 2)

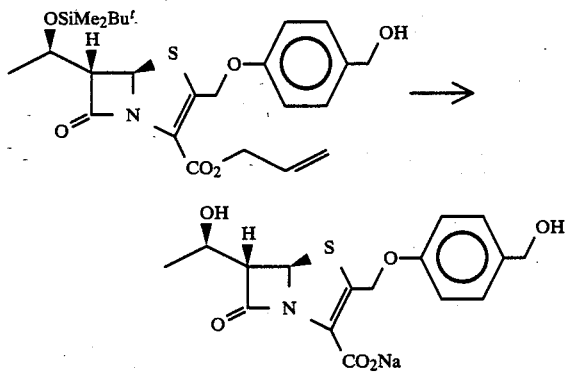

A solution of allyl (5R,6S)-6-8 (1R)-tert-butyldimethylsilyloxyethyl]-2-(4-hydroxymethylphenoxy)methylpenem-3-carboxylate (0.5 g) in tetrahydrofuran (7 ml) was sequentially treated with acetic acid (0.25 ml) and tetrabutylammonium fluoride trihydrate (0.44 g). The mixture was stirred for 15 minutes, then let stand at room temperature for 6 hours. The solvent was removed in vacuo and the residue purified by SiO$_2$ chromatography to obtain the allyl ester of the title product (0.35 g). This material (0.28 g) in a mixture of tetrahydrofuran (5 ml) and dichloromethane (4 ml) was treated under stirring with triphenylphosphine (25 mg) and tetrakis(triphenylphosphine)palladium (0) (25 mg), followed by sodium 2-ethylhexanoate (0.11 g). After stirring for 30 minutes, ethyl ether was added and the precipitate separated by centrifugation. The obtained solid was dissolved in a small amount of water and passed through a reverse-phase column (Merck LiChroprep C-18) eluting with distilled water. Freeze-drying afforded the title product as a white powder (0.15 g);

IR (KBr) $\nu_{max}$ 1770, 1600 cm$^{-1}$.

EXAMPLE 9

Sodium (5R,6S)-6-[(1R)-hydroxyethyl]-2-(4-carbamoyloxymethylphenoxy)methylpenem-3-carboxylate (Compound 1)

Step A

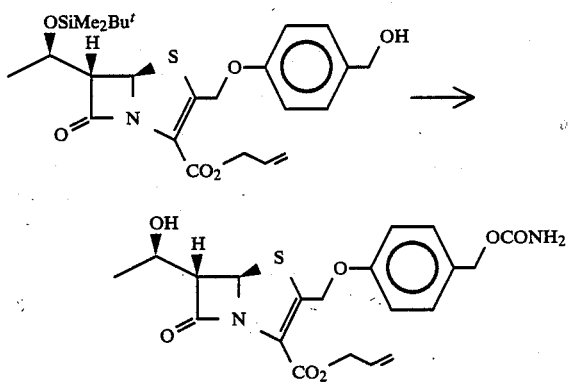

Trichloroacetyl isocyanate (0.15 ml) was added dropwise to a solution of allyl (5R,6S)-6-[(1R)-tert-butyldimethylsilyloxyethyl]-2-(4-hydroxymethylphenoxy)-methylpenem-3-carboxylate (obtained as described in Example 1, Step B) (0.3 g) in cold (−40° C.)dichloromethane. The mixture was let rise to room temperature and then concentrated in vacuo. The residue was dissolved in THF (8 ml) and treated with acetic acid (0.6 ml) and tetrabutylammonium fluoride trihydrate (0.75 g). After 20 hours at room temperature, the solvent was removed and the residue was purified by flash chromatography on silica, thus obtaining allyl (5R,6S)-6-[(1R)-hydroxyethyl]-2-(4-carbamoyloxymethylphenoxy)methylpenem-3-carboxylate (0.25 g) as an amorphous solid.

Step B

The above material (0.2 g) was deallylated with triphenylphosphine and tetrakis(triphenylphosphine)palladium (0) in the presence of sodium ethyl hexanoate as described in Example 8. Reverse phase chromatography afforded the title product (0.13 g);

IR(KBr) $\nu_{max}$ 1760, 1715, 1605 cm$^{-1}$. NMR (200 MHz, D$_2$O) 1.26(3H,d,J=6.3 Hz), 3.79(1H,dd,J=1.6, 5.8 Hz), 4.19(1H,dq,J=5.8, 6.3 Hz), 4.98(2H,s), 5.44 and 5.12 (2H,ABq, J=14.6 Hz), 5.52(1H,d,J=1.6 Hz), 6.97(2H,d,J=8.5 Hz), 7.31(2H,d, J=8.5 Hz)

EXAMPLE 10

Sodium (5R,6S)-6-[(1R)-hydroxyethyl]-2-[4-(1-methyl-1,2,3,4-tetrazol-5-yl)thiomethylphenoxy]methylpenem-3-carboxylate (Compound 4)

Step A

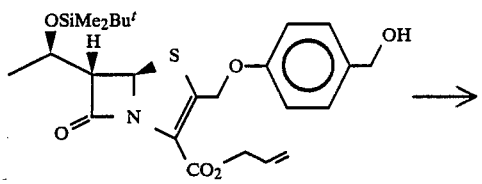

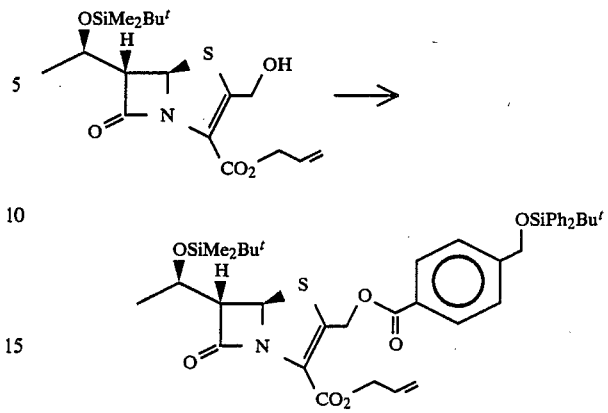

A mixture of triphenylphosphine (700 mg) and diethyl azodicarboxylate (0.42) in dry THF (15 ml), previously stirred at 0° C. for 30 min, was added to a solution of allyl (5R,6S)-6-[(1R)-tert-butyldimethylsilyloxyethyl]-2-(4-hydroxymethylphenoxy)methylpenem-3-carboxylate (400 mg) and 1-methyl-5-mercapto-1,2,3,4-tetrazole (100 mg) in the same solvent (30 ml), while keeping the temperature below +10° C. After 15 min the solvent was removed in vacuo and the residue purified by chromatography on $SiO_2$ (cyclohexane-ethyl acetate), thus obtaining allyl (5R,6S)-6-[(1R)-tert-butyldimethylsilyloxyethyl]-2-[4-(1-methyl-1,2,3,4-tetrazol-5-yl)thiomethylphenoxy]methylpenem-3-carboxylate as a foam (405 mg); IR ($CHCl_3$) $\nu_{max}$ 1790, 1705 cm$^{-1}$.

Step B

From the above material (0.4 g), sequential desilylation and deallylation, by the same methodology described in Example 8, provided the title compound (0.12 g), isolated as an amorphous solid after freeze-drying; IR (KBr) $\nu_{max}$ 1765, 1605 cm$^{-1}$.

EXAMPLE 11

By following the experimental procedure described in Example 10, but replacing 1-methyl-5-mercapto-1,2,3,4-tetrazole with the appropriate nucleophile, i.e. acetic acid, succinimide, uracil, the intermediate allyl (5R,6S)-6-[(1R)-tert-butyldimethylsilyloxyethyl]-2-[4-(hydroxymethyl)phenoxy]methylpenem-3-carboxylate obtained as described in Example 5 was converted, respectively, into:

Sodium (5R,6S)-6-[(1R)-hydroxyethyl]-2-(4-acetoxymethylphenoxy)methylpenem-3-carboxylate (Compound 3);

Sodium (5R,6S)-6-[(1R)-hydroxyethyl]-2-[4-(1-succinimido)methylphenoxy]methylpenem-3-carboxylate (Compound 15);

Sodium (5R,6S)-6-[(1R)-hydroxyethyl]-2-[4-(2,4-dioxo-3-pyrimidinyl)methylphenoxy]methylpenem-3-carboxylate (Compound 16).

EXAMPLE 12

(5R,6S)-6-[(1R)-hydroxyethyl]-2-[4-(1-pyridiniomethyl)benzoyloxy]methylpenem-3-carboxylate (Compound 19)

Step A

Diisopropyl azodicarboxylate (0.2 ml) was added to a cold (0° C.) solution of allyl (5R,6S)-6-[(1R)-tert-butyldimethylsilyloxyethyl]-2-hydroxymethylpenem-3-carboxylate (0.21 g), triphenylphosphine (0.26 g) and 4-(tert-butyldimethylsilyloxymethyl)benzoic acid (0.2 g) in dry tetrahydrofuran (10 ml). After stirring for 15 min, the reaction mixture was taken up ethyl acetate washed with a solution of acetic acid (1 ml) in water (50 ml). The organic layer was further washed with brine, dried ($MgSO_4$), and the solvent was evaporated. Silica gel chromatography afforded allyl (5R,6S)-6-[(1R)-tert-butyldimethylsilyloxyethyl]-2-[4-(tert-butyldiphenylsilyloxymethyl)benzoyloxy]methylpenem-3-carboxylate in almost quantitative yield (400 mg); IR ($CHCl_3$) $\nu_{max}$ 1790, 1720 cm$^{-1}$; NMR (60 MHz, $COCl_3$)δ ppm: 0.1 (6H, s), 0.9 (9H, s), 1.12 (9H, s), 1.20 (3H, d, J=6 Hz), 3.70 (1H, dd, J=2 and 4.5 Hz), 4.2 (1H, m), 4.6–4.8 (4H, m), 5.1–5.6 (2H, m), 5.55 (2H, ABq), 5.65 (1H, d, J=2 Hz), 5.9 (1H, m), 7.3–8.2 (14H, m).

Step B

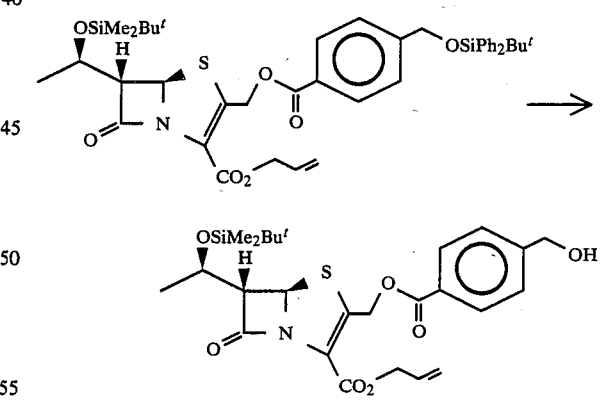

A solution of the product from Step A (400 mg) in tetrahydrofuran (10 ml) was treated with acetic acid (0.1 ml) and tetrabutylammonium fluoride trihydrate (255 mg). After stirring for two hours, the solvent was removed in vacuo and the residue purified by flash-chromatography, thereby obtaining allyl (5R,6S)-6-[(1R)-tert-butyldimethylsilyloxyethyl]-2-[4-(hydroxymethyl)benzoyloxy]methylpenem-3-carboxylate as a pale yellowish, oil (250 mg); IR ($CHCl_3$) $\nu_{max}$ 1790, 1720 cm$^{-1}$; NMR (60 MHz, $CDCl_3$)δ ppm: 0.05 (6H, s), 0.9 (9H, s), 1.2 (3H, d, J=6 Hz), 2.35 (1H, br s), 3.65 (1H, dd, J=2 and 5 Hz), 4.2 (1H, m), 4.65 (4H, m), 5.1–5.5 (2H, m), 5.45 (2H, ABq, J=15 Hz), 5.55 (1H, d, J=2 Hz), 5.9 (1H, m), 7.2–8.1 (4H, m).

Step C

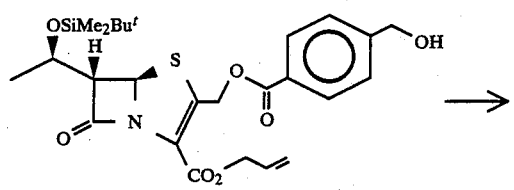

A solution of allyl (5R,6S)-6-[(1R)-tert-butyldimethylsilyloxyethyl]-2-[4-(hydroxymethyl)benzoyloxy]methylpenem-3-carboxylate (250 mg) in dry, ethanol-free dichloromethane (10 ml), was sequentially treated at −40° C. under nitrogen with pyridine (0.25 ml) and trifluoromethanesulphonic anhydride (0.125 ml). Work-up of the reaction mixture and sequential desilylation and deallylation, as described in Example 1, afforded the title compound (60 mg); UV (H$_2$O) $\lambda_{max}$ 236 and 307 nm; IR (KBr) $\gamma_{max}$ 1765, 1720, 1600 cm$^{-1}$; NMR (200 MHz, D$_2$O)δ ppm: 1.27 (3H, d, J=6.3 Hz), 3.79 (1H, dd, J=1.5 and 5.9 Hz), 4.21 (1H, m), 5.07 and 5.74 (2H, each d, J=14.8), 5.51 (1H, d, J=1.5 Hz), 5.92 (2H, s), 7.50 and 7.94 (4H, each d, J=8.4 Hz), 8.14 (1H, dd, J=6.5 and 7.7 Hz), 8.63 (1H, t, J=7.7 Hz), 8.99 (1H, d, J=6.5 Hz).

EXAMPLE 13

By following the experimental procedure described in the above Example 12, but substituting N-methylpyrrolidine for pyridine, there was obtained:

(5R,6S)-6-[(1R)-hydroxyethyl]-2-[4-(1-methyl-1-pyrrolidinio)methylbenzoyloxy]methylpenem-3-carboxylate (Compound 20).

EXAMPLE 14

The intermediate allyl (5R,6S)-6-[(1R)-tert-butyldimethylsilyloxyethyl]-2-[4-(hydroxymethyl)benzoyloxy]methylpenem-3-carboxylate, obtained as described in Example 12, Step B, was treated with trichloroacetyl isocyanate according to the experimental procedure reported in Example 9, thereby obtaining, after removal of the protecting groups:

Sodium (5R,6S)-6-[(1R)-hydroxyethyl]-2-[4-(carbamoyloxymethyl)benzoyloxy]methylpenem-3-carboxylate (Compound 18).

EXAMPLE 15

Likewise, starting from allyl (5R,6S)-6-[(1R)-tert-butyldimethylsilyloxyethyl]-2-[4-(hydroxymethyl)benzoyloxy]methylpenem-3-carboxylate and 1-methyl-5-mercapto-1,2,3,4-tetrazole, and following the experimental procedure described in Example 10, there was obtained:

Sodium (5R,6S)-6-[(1R)-hydroxyethyl]-2-[4-(1-methyl-1,2,3,4-tetrazol-5-yl)thiomethylbenzoyloxy]methylpenem-3-carboxylate (Compound 21).

EXAMPLE 16

(5R,6S)-6-[(1R)-hydroxyethyl]-2-N{4-[(1-pyridinio)methyl]phenyl}carbamoyloxymethylpenem-3-carboxylate (Compound 23).

Step A

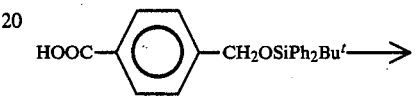

A solution of 4-(tert-butyldiphenylsilyloxy)methylbenzoic acid (2 g) in dry dichloromethane (25 ml) was treated with thionyl chloride (1.1 ml) and dry DMF (3 drops). After stirring for 2 hours at room temperature, any volatile material was removed in vacuo. The crude acid chloride thus obtained was taken up in acetone (25 ml) and mixed under stirring at 0° C. with a solution of sodium azide (0.97 g) in water (4 ml). After few minutes most of the acetone was removed in vacuo and the reaction mixture extracted with benzene. The organic extracts were washed with brine, dried and evaporated to small volume, leaving a concentrated solution of 4-(tert-butyldiphenylsilyloxy)methylbenzoyl azide, which was used as such for the following step; IR (film) 2155, 1705 cm$^{-1}$.

Step B

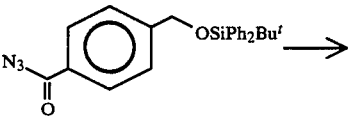

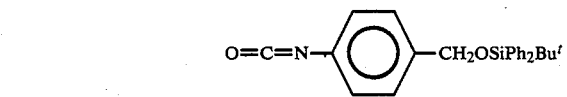

The benzene solution of the acyl azide from the Step A above was refluxed for 4 hours. The solvent was removed in vacuo, thereby obtaining crude 4-(tert-butyldiphenylsilyloxymethyl)phenyl isocyanate; IR (film) $\lambda_{max}$ 2190 cm$^{-1}$.

Step C

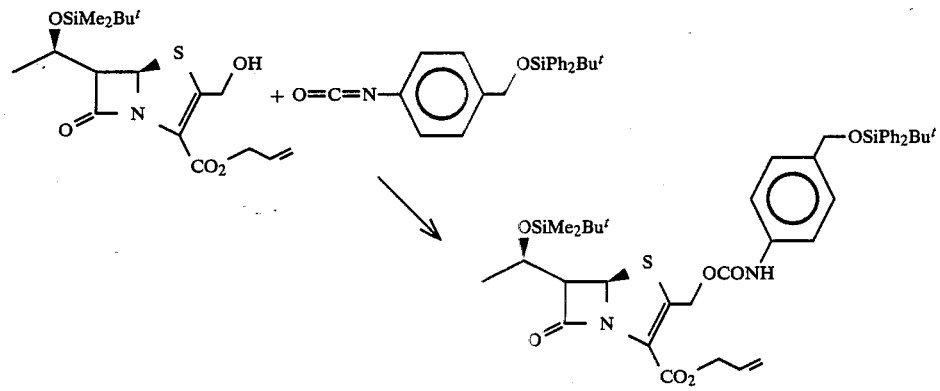

A solution of the crude 4-(tert-butyldiphenylsilyloxymethyl)phenyl isocyanate obtained from step C above (2 g) in ethanol-free chloroform (80 ml) was sequentially treated with allyl (5R,6S)-6-[(1R)-tert-butyldimethylsilyloxyethyl]-2-hydroxymethylpenem-3-carboxylate (2 g) and 4-dimethylaminopyridine (0.06 g). The solution was refluxed for 2 hours, then washed with dilute HCl and water. Removal of the solvent and chromatography afforded allyl (5R,6S)-6-[(1R)-tert-butyldimethylsilyloxyethyl]-2-N-[4-(tert-butyldiphenylsilyloxymethyl)phenyl]carbamoyloxymethylpenem-3-carboxylate (1.9 g).

Step D

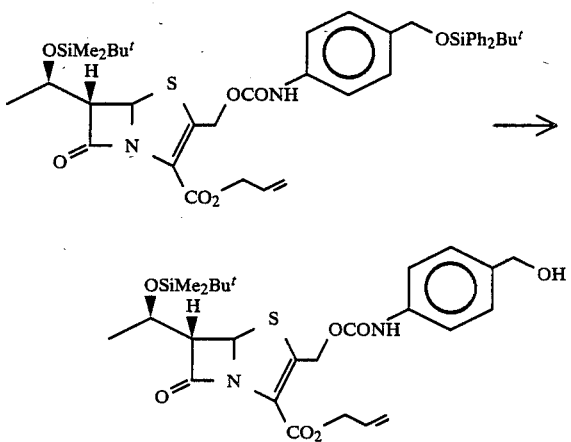

A solution of the bis-silylated product from step C above (1.6 g) in THF (50 ml) was stirred with tetrabutylammonium fluoride trihydrate (0.95 g) and acetic acid (0.35 ml) until TLC (SiO$_2$, ethyl acetate/cyclohexane 1:2) showed almost complete depletion of the starting material. Flash chromatography of the crude product then afforded allyl (5R,6S)-6-[(1R)-tert-butyldimethylsilyloxyethyl]2-N-[4-(hydroxymethyl)phenyl]-carbamoyloxymethylpenem-3-carboxylate (0.6 g).

Step E

Allyl (5R,6S)-6-[(1R)-tert-butyldimethylsilyloxyethyl]-2-N-[4-(hydroxymethyl)phenyl]carbamoyloxymethylpenem-3-carboxylate (0.1 g) in dry CH$_2$Cl$_2$ (10 ml) was sequentially treated with pyridine (0.1 ml) and triflic anhydride (0.05 ml) at $-40°$ C. under argon. After few minutes the reaction mixture was sequentially washed with diluted HCl and brine, and the solvent removed in vacuo. The residue was triturated with ether, and the intermediate pyridinium salt thereby collected (70 mg) was dissolved in THF (5 ml) and acetic acid (0.06 ml), and stirred for 30 h with tetrabutylammonium fluoride trihydrate (95 mg). The crude product obtained from removal of the solvent was poured onto a SiO$_2$ column, which was first eluted with CH$_2$Cl$_2$/MeCN, then with neat MeCN, then with MeCN/H$_2$O. The desilylated intermediate was extracted from the last fractions by washing with brine and evaporation of the organic layer. This material (50 mg) in THF/CH$_2$Cl$_2$ (1 ml each) was treated with acetic acid (0.1 ml), triphenylphosphine (50 mg) and tetrakis(triphenylphosphine)Pd° (50 mg). After 15 min ethyl ether was added and the precipitate was collected, dissolved in water and passed through a LiChroprep RP-18 column, eluting with water and then with MeCN/water. Freeze-drying of the appropriate fractions afforded the title product, 25 mg; NMR (200 MHz, D$_2$O)δ 1.24(3H,d,J=6.4 Hz), 3.82 (1H,dd,J=1.6 and 5.8 Hz), 4.18(1H,dq,J=5.8 and 6.4 Hz), 5.05 and 5.42(2H,ABq,J=14.6 Hz), 5.55(1H,d,J=1.6 Hz), 5.75(2H,m), 7.43(4H,m), 8.05(2H,m), 8.53(1H,m), 8.89(2H,m).

EXAMPLE 17

Sodium (5R,6S)-6-[(1R)-hydroxyethyl]-2-N-[4-(carbamoyloxymethyl)phenyl]carbamoyloxymethylpenem-3-carboxylate (Compound 22)

The title product was obtained starting from allyl (5R,6S)-6-[(1R)-tert-butyldimethylsilyloxyethyl]-2-N-[4-(hydroxymethyl)phenyl]carbamoyloxymethylpenem-3-carboxylate, described in Example 16, step D, and trichloroacetyl isocyanate, by following the procedure reported in Example 9.

EXAMPLE 18

(5R,6S)-6-[(1R)-hydroxyethyl]-2-N-{4-[(1-methylpyrrolidinio)methyl]phenyl}carbamoyloxymethylpenem-3-carboxylate (Compound 24)

The title product was obtained as described in Example 16 by substituting N-methylpyrrolidine for pyridine.

EXAMPLE 19

(5R,6S)-6-[(1R)-hydroxyethyl]-2-[4-(3,5-dimethyl-1-pyridinio)methylphenyl]oxymethylpenem-3-carboxylate (Compound 31)

A solution of allyl (5R,6S)-6-[(1R)-trimethylsilyloxyethyl]-2-[4-(bromomethyl)phenyl]oxymethylpenem-3-carboxylate (0.1 g) in dry DMF (2 ml) was stirred overnight with 3,5-dimethylpyridine (0.15 ml). The solvent was removed in vacuo and the residue triturated with ether to leave a yellowish solid (0.1 g), which was stirred for 30 min in THF/water/acetic acid (6:2:1, 9 ml). The mixture was evaporated to dryness to afford the crude allyl ester of the title product, which was then obtained by Pd-catalyzed deallylation, as described in Example 1; IR(KBr) $\nu_{max}$ 1765, 1605 cm$^{-1}$; UV(H O) $\lambda_{max}$ 308 nm

EXAMPLE 20

By following the experimental procedure described in the above Example 19 and replacing 3,5-dimethylpyridine with 3-hydroxypyridine, sodium 4-pyridineethansulphonate, 3-hydroxymethylpyridine, 2-(2-hydroxyethyl)pyridine, 8-hydroxyquinoline, 8-hydroxyisoquinoline, 3-formylaminopyridine, isonicotinohydroxamic acid, 3-pyridinecarboxaldehyde, 3-pyridinealdoxime, 4-acetylpyridine oxime, 3-aminopyridine, pyrazine, 1-methyl-1,2,3-triazole, 1-methylpyrazole, thieno[2,3-c]pyridine, furo[2,3-c]pyridine, furo[3,2-c]pyridine, thieno[3,2-c]pyridine, thieno[2,3-b]pyridine, furo[2,3-b]pyridine, thieno[3,4-c]pyridine, and thiazolo[4,5-c]pyridine, there were obtained, respectively, (5R,6S)-6-[(1R)-hydroxyethyl]-2-[4-(3-hydroxy-1-pyridinio)methylphenyl]oxymethylpenem-3-carboxylate (Compound 32);
IR (KBr) $\gamma_{max}$ 1763 1600 cm$^{-1}$.
UV (H$_2$O) $\lambda_{max}$ 256 and 307 nm.
(5R,6S)-6-[(1R)-hydroxyethyl]-2-[4-(4-sulphoethyl-1-pyridinio)methylphenyl]oxymethylpenem-3-carboxylate (Compound 33);
IR (KBr) $\gamma_{max}$ 1765.
UV (H$_2$O) $\lambda_{max}$ 308 nm.
(5R,6S)-6-[(1R)-hydroxyethyl]-2-[4-(3-hydroxymethyl-1-pyridinio)methylphenyl]oxymethylpenem-3-carboxylate (Compound 34);
(5R,6S)-6-[(1R)-hydroxyethyl]-2-[4-(2-hydroxyethyl-1-pyridinio)methylphenyl]oxymethylpenem-3-carboxylate (Compound 35);
(5R,6S)-6-[(1R)-hydroxyethyl]-2-[4-(8-hydroxy-1-quinolinio)methylphenyl]oxymethylpenem-3-carboxylate (Compound 36);
(5R,6S)-6-[(1R)-hydroxyethyl]-2-[4-(8-hydroxy-2-isoquinolinio)methylphenyl]oxymethylpenem-3-carboxylate (Compound 37);
(5R,6S)-6-[(1R)-hydroxyethyl]-2-[4-(3-formylamino-1-pyridinio)methylphenyl]oxymethylpenem-3-carboxylate (Compound 38);
(5R,6S)-6-[(1R)-hydroxyethyl]-2-[4-(4-hydroxyaminocarbonyl-1-pyridinio)methylphenyl]oxymethylpenem-3-carboxylate (Compound 39);
(5R,6S)-6-[(1R)-hydroxyethyl]-2-[4-(3-formyl-1-pyridinio)methylphenyl]oxymethylpenem-3-carboxylate (Compound 40);
(5R,6S)-6-[(1R)-hydroxyethyl]-2-[4-(3-hydroxyiminomethyl-1-pyridinio)methylphenyl]oxymethylpenem-3-carboxylate (Compound 41);
(5R,6S)-6-[(1R)-hydroxyethyl]-2-{4-[(1-hydroxyiminoethyl)-1-pyridinio]methylphenyl}oxymethylpenem-3-carboxylate (Compound 42);
(5R,6S)-6-[(1R)-hydroxyethyl]-2-[4-(3-amino-1-pyridinio)methylphenyl]oxymethylpenem-3-carboxylate (Compound 43);
(5R,6S)-6-[(1R)-hydroxyethyl]-2-[4-(1-pyrazinio)methylphenyl]oxymethylpenem-3-carboxylate (Compound 44);
(5R,6S)-6-[(1R)-hydroxyethyl]-2-[4-(1-methyl-1-triazolio)methylphenyl]oxymethylpenem-3-carboxylate (Compound 45);
(5R,6S)-6-[(1R)-hydroxyethyl]-2-[4-(2-methyl-1-pyrazolio)methylphenyl]oxymethylpenem-3-carboxylate (Compound 46);
(5R,6S)-6-[(1R)-hydroxyethyl]-2-[4-(thieno[2,3-c]pyridinio)methylphenyl]oxymethylpenem-3-carboxylate (Compound 47);
(5R,6S)-6-[(1R)-hydroxyethyl]-2-[4-(furo[2,3-c]pyridinio)methylphenyl]oxymethylpenem-3-carboxylate (Compound 48);
(5R,6S)-6-[(1R)-hydroxyethyl]-2-[4-(furo[3,2-c]pyridinio)methylphenyl]oxymethylpenem-3-carboxylate (Compound 49);
(5R,6S)-6-[(1R)-hydroxyethyl]-2-[4-(thieno[3,2-c]pyridinio)methylphenyl]oxymethylpenem-3-carboxylate (Compound 50);
(5R,6S)-6-[(1R)-hydroxyethyl]-2-[4-(thieno[2,3-b]pyridinio)methylphenyl]oxymethylpenem-3-carboxylate (Compound 51);
(5R,6S)-6-[(1R)-hydroxyethyl]-2-[4-(furo[2,3-b]pyridinio)methylphenyl]oxymethylpenem-3-carboxylate (Compound 52);
(5R,6S)-6-[(1R)-hydroxyethyl]-2-[4-(thieno[3,4-c]pyridinio)methylphenyl]oxymethylpenem-3-carboxylate (Compound 53); and
(5R,6S)-6-[(1R)-hydroxyethyl]-2-[4-(thiazolo[4,5-c]pyridinio)methylphenyl]oxymethylpenem-3-carboxylate (Compound 54).

EXAMPLE 21

(5R,6S)-6-[(1R)-hydroxyethyl]-2-[4-(1-pyridinio)methylphenoxy]carbonyloxymethylpenem-3-carboxylate (Compound 25)

A solution of allyl (5R,6S)-6-[(1R)-tert-butyldimethylsilyloxyethyl]-2-hydroxymethylpenem-3-carboxylate (400 mg) in dry dichloromethane (20 ml) was treated at −10° C. under nitrogen with 4-(tert-butyldiphenylsilyloxymethyl)phenyl chlorocarbonate (500 mg) and triethylamine (0.2 ml). The reaction mixture was warmed up to room temperature, washed with aq. NaHCO$_3$, dried and evaporated. Silica gel chromatography afforded allyl (5R,6S)-6-[(1R)-tert-butyldimethylsilyloxyethyl]-2-[4-(tert-butyldiphenylsilyloxy)methylphenoxy]carbonyloxymethylpenem-3-carboxylate (0.6 g). A solution of this product in THF (20 ml) was stirred for 8 h in the presence of acetic acid (0.4 ml) and tetrabutylammonium fluoride trihydrate (0.4 g). The solvent was removed in vacuo and the residue fractionated through a silica gel column (n-hexane/ethyl acetate) to give allyl (5R,6S)-6-[(1R)-tert-butyldimethylsilyloxyethyl]-2-(4-hydroxymethylphenoxy)carbonyloxymethylpenem-3-carboxylate (0.35 g).

The above material was sequentially reacted with pyridine/triflic anhydride, desilylated and deallylated, by following the experimental procedure described in Example 1, step C, thereby obtaining the title product as an amorphous solid (75 mg); IR(KBr) $\nu_{max}$ 1765, 1750, 1600 cm$^{-1}$; UV(H$_2$O) $\lambda_{max}$ 307 nm.

EXAMPLE 22

(5R,6S)-6-[(1R)-hydroxyethyl]-2-[4-(1-pyridinio)methylphenyl]thiomethylpenem-3-carboxylate (Compound 26)

A solution of 4-methylthiobenzaldehyde (15.2 g) in methanol (200 ml) was treated at 0° C. with sodium borohydride (3.8 g). After neutralization with HCl, the reaction mixture was concentrated and partitioned between EtOAc and brine. Removal of the solvent afforded 4-methylthiobenzyl alcohol. This material (13.3 g) was treated with m-CPBA (15.5 g) in CHCl$_3$ (300 ml) at 0° C. After 30 min, the solution was washed with aq. NaHCO$_3$ and evaporated, to afford 4-methylsulphinylbenzyl alcohol. This product (7.9 g) in dry dichloromethane (100 ml) was treated with trifluoromethanesulphonic anhydride (19.5 ml) and refluxed for 30 min. The reaction mixture was poured into ethanolic NaOH and then worked up to afford crude 4-mercaptobenzyl alcohol, a solution of which in chloroform was directly oxidized with an aqueous solution of KI (added dropwise until a persistent colour resulted). After washing with NaHSO$_3$ and brine, removal of the solvent afforded 4-hydroxymethylphenyl disulfide. This material (3 g) was treated with tert-butyldiphenyl silyl chloride (6.5 ml) and imidazole (5 g) in dry dimethylformamide. After 2 h at room temperature, work-up and chromatography afforded 4-tert-butyldiphenylsilyloxymethylphenyl disulfide (5.5 g) as a syrup. Immediately before use, the above disulfide (1 g) was reduced to 4-(tert-butyldiphenylsilyloxymethyl)thiophenol by brief treatment with Zn powder (1 g) in acetic acid -dichloromethane (20 ml each). The crude mercaptane thereby obtained was coupled with allyl (5R,6S)-6-[(1R)-tert-butyldimethylsilyloxyethyl]-2-hydroxymethylpenem-3-carboxylate, under the conditions described in Example 1, Step B. The resulting allyl (5R,6S)-6-[(1R)-tert-butyldimethylsilyloxyethyl]-2-(4-hydroxymethylphenyl)thiomethylpenem-3-carboxylate was treated with pyridine/triflic anhydride, desilylated and deallylated, according to the experimental procedure described in Example 1, thus obtaining the title product; IR $\nu_{max}$(KBr) 3300, 1765, 1600 cm$^{-1}$.

EXAMPLE 23

(5R,6S)-6-[(1R)-hydroxyethyl]-2-[4-(1-pyridinio)methylphenyl]sulfinylmethylpenem-3-carboxylate (Compound 27)

Allyl (5R,6S)-6-[(1R)-tert-butyldimethylsilyloxyethyl]-2-[4-(1-pyridinio)methylphenyl]thiomethylpenem-3-carboxylate, obtained (as the trifluoromethanesulfonate salt) as an intermediate in the process described in the previous Example 22, was dissolved in dichloromethane at −20° C. and treated with 1 mol equiv. of 3-chloro peroxybenzoic acid. After depletion of the starting material, dimethylsulfide was added, the mixture was warmed up to room temperature and the solvent removed in vacuo. Sequential desilylation and deallylation, performed as described in Example 1, afforded the title product; IR $\nu_{max}$ 1760, 1600 cm$^{-1}$.

EXAMPLE 24

(5R,6S)-6-[(1R)-hydroxyethyl]-2-[4-(1-pyridinio)methylphenyl]sulfonylmethylpenem-3-carboxylate (Compound 30)

A solution of sodium 4-(hydroxymethyl)phenylsulfinate in dry THF was stirred overnight with 1 mol equiv. of allyl (5R,6S)-6-[(1R)-tert-butyldimethylsilyloxyethyl]-2-chloromethylpenem-3-carboxylate.

The reaction mixture was partitioned between water and ethyl acetate, and the residue from the dried organic layer was purified by silica gel chromatography to obtain allyl (5R,6S)-6-[(1R)-tert-butyldimethylsilyloxyethyl]-2-(4-hydroxymethylphenyl)sufonylmethylpenem-3-carboxylate. Treatment of this material with pyridine/triflic anhydride, followed by sequential desilylation and deallylation, according to the procedure described in Example 1, afforded the title product; IR $\nu_{max}$ 1765, 1605 cm$^{-1}$.

EXAMPLE 25

By sequential exposure to trichloroacetylisocyanate and deblocking of the protective groups, according to the procedure described in Example 9, allyl (5R,6S)-6-[(1R)-tert-butyldimethylsilyloxyethyl]-2-(4-hydroxymethylphenyl)sulfinylmethylpenem-3-carboxylate and allyl (5R,6S)-6-[(1R)-tert-butyldimethylsilyloxyethyl]-2-(4-hydroxymethylphenyl)sulfonylmethylpenem-3-carboxylate were converted into, respectively, sodium (5R,6S)-6-[(1R)-hydroxyethyl]-2-(4-carbamoyloxymethylphenyl)sulfinylmethylpenem-3-carboxylate (Compound 28), and sodium (5R,6S)-6-[(1R)-hydroxyethyl]-2-(4-carbamoyloxymethylphenyl)sulfonylmethylpenem-3-carboxylate (Compound 29).

EXAMPLE 26

By following the experimental procedure described in Example 19 but replacing 3,5-dimethylpyridine with the appropriate pyridine sulphonic acids (as their sodium salts), there were obtained:

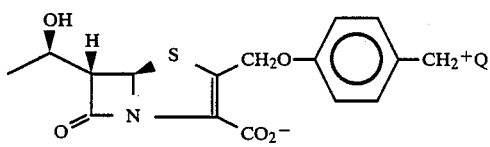

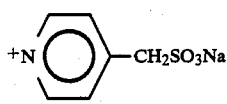
(Compound 54/A)

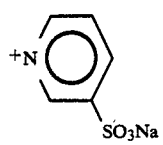
(Compound 55)

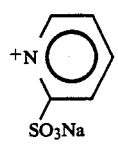
(Compound 56)

EXAMPLE 27

(5R, 6S)-6-[(1R)-hydroxyethyl]-2-[4-(4-carboxy-1-pyridinio)methylphenyl]-oxymethylpenem-3-carboxylate (Compound 57)

Step A:
Protection of the carboxyl function present in the reactant.

To a supsension of isonicotinic acid (6.15 g) in dry DMF (100 ml), triethylamine (8.4 ml) was added, and the resulting solution was stirred overnight in the presence of allyl bromide (5.1 ml). The reaction mixture was partitioned between water and ethyl acetate, and the organic layer was separated, washed with brine, dried over Na$_2$SO$_4$ and evaporated in vacuo to yield 4 allyloxycarbonylpiridine (3.1 g) as a colourless oil. NMR (90 MHz, CDCl$_3$)δ ppm 4.77 (2H, m), 5.24 (1H, d, J=10 Hz), 5.37 (1H, d, J=12 Hz), 5.94 (1H, m), 7.80 (2H, m), 8.70 (2H, m).

Step B:
Condensation with allyl (5R, 6S)-6-[(1R)-hydroxyethyl]-2-(4-bromomethylphenyl)oxymethylpenem-3-carboxylate.

The title bromomethylphenyl intermediate (600 mg) was stirred overnight with 4-allyloxycarbonylpyridine (800 mg) in dry DMF.

After removal of the solvent under hight vacuum, the residue was taken up in dichloromethane and dropped into ethyl ether. The precipitate was collected (560 mg) and used as such for the following step.

Step C:
Removal of the protecting groups.

The crude allyl (5R, 6S)-6-[(1R)-hydroxyethyl]-2-[4-(4-allyloxycarbonyl-1-pyridinio)-methylphenyl]oxymethylpenem-3-carboxylate (bromide salt) obtained in the previous step was stirred for 30 minutes with triphenylphosphire (250 mg) and Pd(Ph$_3$P)$_4$ (250 mg) o, acetonitrile (50 ml) and acetic acid (5 ml). A further amount of PPh$_3$ and Pd (Ph$_3$P)$_4$ (250 mg each) was then added and the mixture was stirred for 30 minutes, after which time was diluted with ethyl ether (190 ml). The precipitated solid was collected by filtration, washed with ether, dissolved in aqueous NaHCO$_3$ and chromatographed on LiChroprep RP-18 eluting first with water and than with acetone-water.

The appropriate fractions were combined and freeze-dried to afford 240 mg of the title compound as a white powder;

NMR (200 MHz, D$_2$O) 1.31 (3H, d, J=6.6 Hz), 3.98 (1H, d, J=1.6 and 6.0 Hz), 4.26 (1H, dq, J=6.0 and 6.6 Hz), 5.28 (2H, ABq), 5.77 (1H, d, J=1.6 Hz), 5.84 (2H, s), 7.46 (4H, m), 8.25 (2H,m), 8.96 (2H,m); UV (H$_2$O) λ$_{max}$ 308 nm; IR (KBr) ν$_{max}$ 1765, 1630 cm$^{-1}$.

EXAMPLE 28

By following the experimental procedure described in Example 27, but replacing isonicotinic acid with the appropriately substituted pyridines or tertiary amines, there were obtained:

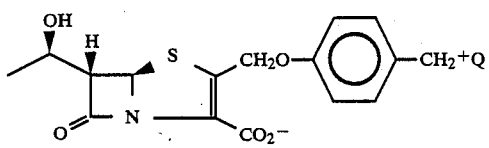
(Compound 58)

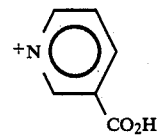
(Compound 59)

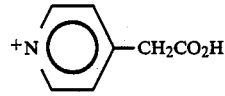
(Compound 60)

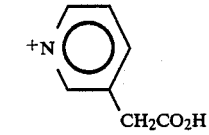
(Compound 61)

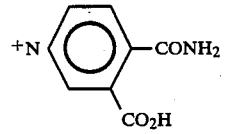
(Compound 62)

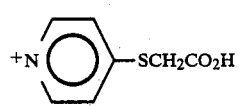
(Compound 63)

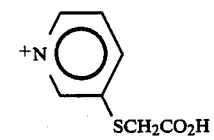
(Compound 64)

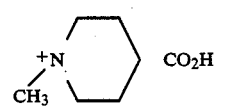
(Compound 65)

-continued

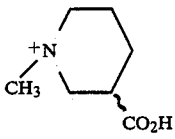 (Compound 66)

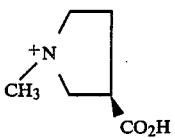 (Compound 67)

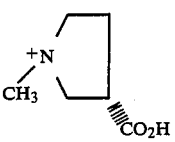 (Compound 68)

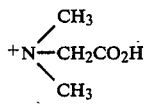 (Compound 69)

EXAMPLE 29

(5R, 6S)-6-[(1R)-hydroxyethyl]-2-[4-(4-dimethylamino-1-pyridinio)-methylphenyl]oxymethylpenem-3-carboxylate (Compound 70)

A solution of 4-dimethylaminopyridine (1 g) and allyl (5R, 6S)-6-[(1R)-hydroxyethyl]-2-(4-bromomethylphenyl)oxymethylpenem-3-carboxylate (550 mg) in dry DMF (5 ml) was stirred at room temperature for 12 hours. The solvent was distilled off under high vacuum and the residue was triturated with ethyl ether to obtain a gummy precipitate of the allyl ester (bromide salt) of the title product. Without further purification, this material was dissolved in 50 ml of dichloromethane, and acetic acid (1 ml), triphenylphosphine (0.25 g) and tetrakis (triphenylphosphine) Pd (O) (0.25 g) were added in that order. After stirring for 30 minutes, the reaction mixture was concentrated and the residue was triturated with ethyl acetate. The obtained solid was dissolved in demineralized water and chromatographed on LiChroprep RP-18 eluting first with water and then with 10% CH₃CN in water. Freeze-drying of the appropriate fractions afforded the title compound (270 mg) as a white powder.

UV (H₂O) $\lambda_{max}$ 307 nm.
IR (KBr) $\lambda_{max}$ 1760, 1600 cm$^{-1}$.

EXAMPLE 30

By following the experimental procedure described in Example 29, but replacing 4-dimethylaminopyridine with the appropriately substituted pyridines, or with 1,4-dimethympiperazine, there were obtained:

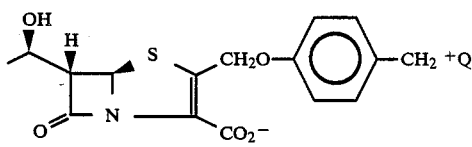

Q⁺ =

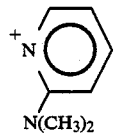 (Compound 71)

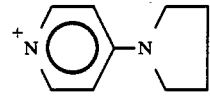 (Compound 72)

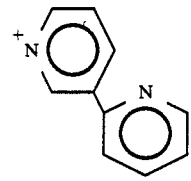 (Compound 73)

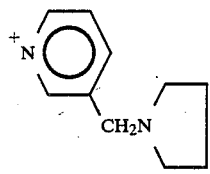 (Compound 77)

 (Compound 79)

EXAMPLE 31

(5R, 6S)-6-[(1R)-hydroxyethyl]-2-[4-(1-methyl-1-piperazinio) methylphenyl]oxymethylpenem-3-carboxylate (Compound 78)

Step A:
Protection of the NM functionality present in the reactant.

A solution of allyl chloroformate (15 ml) in dry dichloromethane was added at −20° C. under stirring to a solution of N-methylpiperazine (10 g) in the same solvent. After 30 minutes the temperature was let rise to +15° C. and the reaction mixture was poured into water. The organic layer was discarded, 1N NaOH was added to a pH≧7, and the mixture was extracted with dichloromethane. The CH₂Cl₂ extracts were dried (MgSO₄), evaporated, and the resulting oil distilled 118° C. (at 18 mmHg) to yield 4-allyloxycarbonyl-1-methylpiperazine (15.3 g).

Step B:
Condensation with allyl (5R, 6S)-6-[(1R)-hydroxyethyl]-2-(4-bromomethylphenyl)oxymethylpenem-3-carboxylate.

Condensation of the title intermediate with the above 4-allyloxycarbonyl-1-methylpiperazine was carried out as described in Example 27, step B.

Step C:
Removal of the protecting groups.

The crude allyl (5R, 6S)-6-[(1R)-hydroxyethyl]-2-[4-(4-allyloxycarbonyl-1-methylpiperazinio)methylphenyl]oxymethylpenem-3-carboxylate bromide obtained in the previous step was treated with PPh$_3$/Pd(PPh$_3$)$_4$/HOAc under the conditions described in Example 27, step C. Purification by reverse-phase chromatography (Lichroprep RP-18) and freeze drying afforded the title compound:

IR (KBr) $\gamma_{max}$ 1765, 1600 cm$^{-1}$;
UV (H$_2$O) $\lambda_{max}$ 308 nm

EXAMPLE 32

By following the experimental procedure described in Example 31, but replacing 1-methylpiperazine with the appropriate (aminomethyl) pyridines, there were obtained:

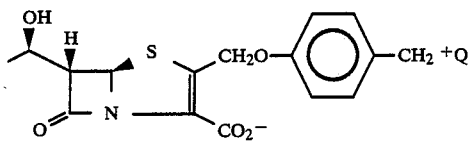

Q$^+$ =

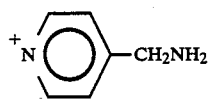
(Compound 74)

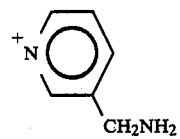
(Compound 75)

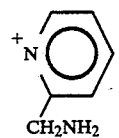
(Compound 76)

We claim:
1. A compound of the following formula I:

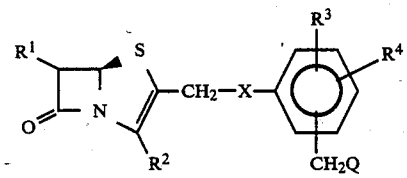

wherein
R$^1$ is hydrogen or a C$_1$-C$_4$ alkyl group either unsubstituted or substituted by one or more substituents chosen from a free or protected hydroxy or halogen atom;
R$^2$ is a free or esterified carboxy group or carboxylate anion;
R$^3$ and R$^4$ are each independently either hydrogen or
(a) a C$_1$-C$_6$ alkyl group, or R$^3$ and R$^4$ are two ortho alkyl groups linked to form a di- to decamethylene ring or a decamethylene ring in which one ring C atom is replaced by N, O or S, or said decamethylene ring containing one or two double bonds, or
(b) a C$_2$-C$_6$ alkenyl group, or
(c) a C$_2$-C$_6$ alkynyl group, or
(d) a C$_1$-C$_6$ alkylsulphinyl group or alkylsulphonyl group, or (e) a C$_1$-C$_6$ alkanoyl group, or
(f) halogen, —CF$_3$, —CN, —CHO, or —CONH$_2$, or
(g) OR, SR or NHR, wherein R represents hydrogen atom or a C$_1$-C$_6$ alkyl or C$_1$-C$_6$ alkanoyl group;
X is either
(a') an oxygen atom, or
(b') a sulphinyl group

or
(c') a sulphonyl group

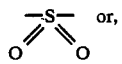

or,
(d') a sulphur atom;
Q is either
(a'') free or protected hydroxy, or
(b'') a C$_1$-C$_4$ acyloxy, or
(c'') carbamoyloxy OCONH$_2$, or
(d'') a
heterocyclythio group wherein the heterocyclic moiety of the heterocyclic thio group is a saturated or unsaturated, monocyclic or bicyclic ring, containing from 1 to 5 heteroatoms selected from oxygen, nitrogen and sulphur, or
(e'') an imido group which is a five or six-membered cyclic imido group having the structural formula

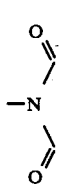

or said structural formula incorporating, in addition to the imido nitrogen, one or two heteroatoms selected from nitrogen, oxygen and sulphur, or said cyclic imido group fused with a benzene or pyridine ring, or
(f'') a quaternary ammonium group the quaternary ammonium group being of the formula

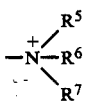

wherein
(1) R$^5$, R$^6$, R$^7$ are each independently an alkyl, aralkyl or aryl radical; or
(2) R$^5$ is as defined above under (1) and R$^6$, R$^7$ taken together with the nitrogen atom represent a heterocyclic radical, or such radical fused with one phenyl ring or with a 5-7 membered, saturated or unsaturated cycloaliphatic or heterocyclic ring; or
(3) R$^5$, R$^6$, R$^7$, taken together with the nitrogen atom, represent an azoniabicyclo or azoniotricyclo radical; or
(4) R$^5$, R$^6$, R$^7$ taken together with the nitrogen atom, represent a pyridinium, pyrazolium, pirazinium, or pyridazinium radical, or such radical fused with one phenyl ring or with a 5-7 membered, saturated or unsaturated cycloaliphatic or heterocyclic ring, or (g") a halogen atom,
or such groups $R^3$, $R^4$, X and Q in which the alkyl, alkenyl, alkynyl, cycloalkyl, alkylamino, alkoxy, alkylthio, alkylsulphinyl, alkylsulphonyl, alkanoyl groups under (a)-(g), the heterocyclythio group under (d") the imido group under (e"), and the $R^5$, $R^6$, $R^7$ radicals of the ammonium group as defined above, are independently substituted by a substituent selected from the class consisting of (a''') halogen, (b''') hydroxy, (c''') $C_1$-$C_4$ alkoxy, (d''') $C_1$-$C_4$ alkylthio, (e) amino, or amino mono- or disubstituted with $C_1$-$C_4$ alkyl groups, (f''') sulfo, (g''') free or esterified carboxy, ((h''') —$CONH_2$ or CN, (k''') carbamoyloxy, or hydroxycarbamoyl (l''') hydroxyminomethyl (HO—N=CH), α-methylhydroxyiminomethyl (HO—N=C($CH_3$)—) or methoxyiminomethyl ($CH_3$—O—N=CH—), (m''') formamido or acetamido, (n''') formyloxy or acetoxy, (o''') $C_1$-$C_6$ alkanoyl group, (p''') nitro, (q''') $C_1$-$C_4$ alkyl group either unsubstituted or substituted by a substituent chosen from (a''') to (p''') above, and the pharmaceutically or veterinarily acceptable salts thereof.

2. A compound of formula (I) as defined in claim 1 wherein $R^1$ is an α-hydroxyethyl group.

3. A compound according to claims 1 or 2 wherein $R^3$ and $R^4$ are hydrogen, or each independently are hydrogen, hydroxy, formyloxy, acetoxy, carbamoyloxy; or $R^3$ and $R^4$ taken together are —CH=CH—CH=CH—.

4. A compound according to any one of the preceding claims, wherein Q represents hydroxy, acetoxy $OCOCH_3$, or carbamoyloxy $OCONH_2$, group.

5. A compound according to claim 4, which is chosen from: sodium (5R,6S)-6-[(1R)-hydroxyethyl]-2-(4-carbamoyloxyphenoxy)methypenem-3-carboxylate; sodium (5R,6S)-6-[(1R)-hydroxyethyl]-2-(4-hydroxymethylphenoxy)methylpenem-3-carboxylate; sodium (5R,6S)-6-[(1R)-hydroxyethyl]-2-(4-acetoxymethylphenoxy)methyl-penem-3-carboxylate; sodium (5R,6S)-6-[(1R)-hydroxyethyl]-2-[4-(carbamoyloxymethyl)benzoyloxy]methylpenem-3-carboxylate; sodium (5R,6S)-6-[(1R)-hydroxyethyl]-2-(4-carbamoyloxymethylphenyl)sulfinylmethylpenem-3-carboxylate; sodium (5R,6S)-6-[(1R)-hydroxyethyl]-2-(4-carbamoyloxymethylphenyl)sulfonylmethylpenem-3-carboxylate.

6. A compound according to claims 1, 2 or 3, wherein Q represents a heterocyclylthio group selected from the following:

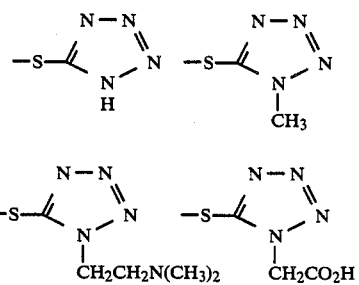

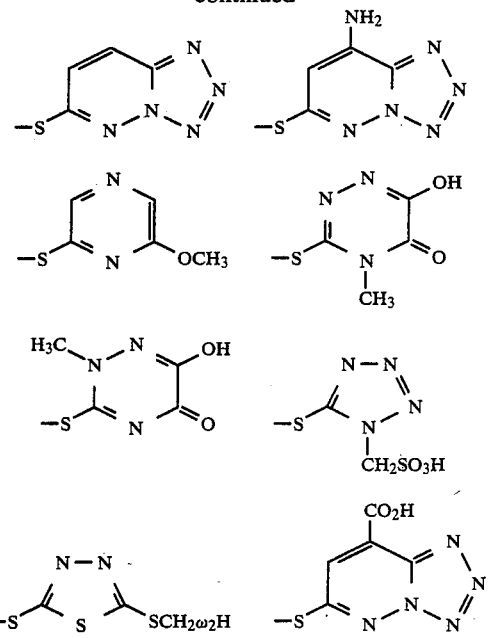

7. A compound according to claim 6, which is chosen from: sodium (5R,6S)-6-[(1R)-hydroxyethyl]-2-[4-(1-methyl-1,2,3,4-tetrazol-5-yl)thiomethylphenoxy]methylpenem-3-carboxylate.

8. A compound according to claim 1, 2 or 3, wherein Q represents an imido group selected from the following

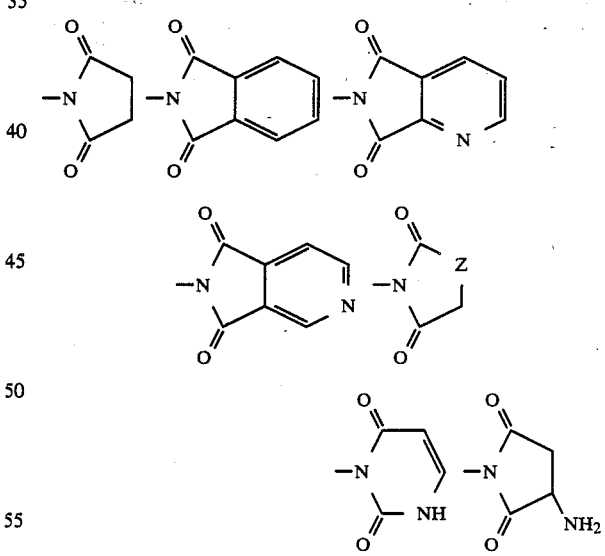

wherein Z represents oxygen or sulphur atom or an imine group.

9. A compound according to claim 8, which is chosen from: sodium (5R,6S)-6-[(1R)hydroxyethyl]-2-[4-(1-succinimido)methylphenoxy]methylpenem-3-carboxylate; sodium (5R,6S)-6-[(1R)-hydroxyethyl]-2-[4-(2,4-dioxo-3-pirimidinyl)methylphenoxy]methylpenem-3-carboxylate.

10. A compound according to claims 1, 2 or 3, wherein Q represents an ammonium group selected from the following:

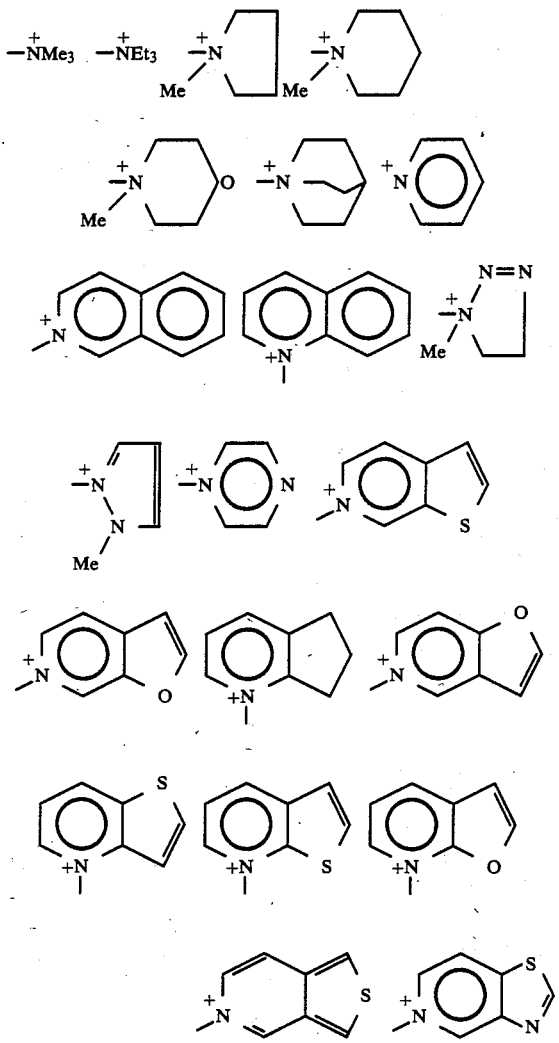

wherein the pyridinium, quinolinium, isoquinolinium, pyrazinium, thieno[2,3-c]pyridium, furo[2,3-c]pyridinium, furo[3,2-c]pyridinium, thieno[3,2-c]pyridinium, thieno[2,3-b]pyridinium, furo[2,3-b]pyridinium, thieno[3,4-c]pyridinium, and thiazolo[4,5-c]pyridinium rings are either unsubstituted or substituted by one or two substituents selected from $C_1$–$C_4$ alkoxy, cyano-$C_1$–$C_4$ alkyl, $C_1$–$C_4$ alkyl, hydroxy, sulpho-$C_1$–$C_4$ alkyl, hydroxy-$C_1$–$C_4$-alkyl, formylamino, formyl, hydroxyimino-$C_1$–$C_4$ alkyl and amino groups.

11. A compound according to claim 10 which is chosen from:

(5R,6S)-6-[(1R)-hydroxyethyl]-2-[4-(1-pyridinio)methylphenyl]oxymethylpenem-3-carboxylate;

(5R,6S)-6-[(1R)-hydroxyethyl]-2-[3-(1-pyridinio)methylphenoxy]methylpenem-3-carboxylate;

(5R,6S)-6-[(1R)-hydroxyethyl]-2-[2-(1-pyridinio)methylphenoxy]methylpenem-3-carboxylate;

(5R,6S)-6-[(1R)-hydroxyethyl]-2-[4-(2,3-cyclopenteno-1-pyridinio)methylphenyl]oxymethylpenem-3-carboxylate;

(5R,6S)-6-[(1R)-hydroxyethyl]-2-[4-(1-methyl-1-pyrrolidinio)methylphenyl]oxymethylpenem-3-carboxylate;

(5R,6S)-6-[(1R)-hydroxyethyl]-2-[4-(1-methyl-1-piperidinio)methylphenyl]oxymethylpenem-3-carboxylate;

(5R,6S)-6-[(1R)-hydroxyethyl]-2-[4-(3-methoxy-1-pyridinio)methylphenyl]oxymethylpenem-3-carboxylate;

(5R,6S)-6-[(1R)-hydroxyethyl]-2-[4-(3-cyanomethyl-1-pyridinio)methylphenyl]oxymethylpenem-3-carboxylate;

(5R,6S)-6-[(1R)-hydroxyethyl]-2-[4-(4-methyl-4-morpholinio)methylphenyl]oxymethylpenem-3-carboxylate;

(5R,6S)-6-[(1R)-hydroxyethyl]-2-[4-(1-quinuclidinio)methylphenyl]oxymethylpenem-3-carboxylate;

(5R,6S)-6-[(1R)-hydroxyethyl]-2-[2-hydroxy-4-(1-pyridinio)methylphenoxy]methylpenem-3-carboxylate;

(5R,6S)-6-[(1R)-hydroxyethyl]-2-[4-(1-pyridinio)methylphenyl]thiomethylpenem-3-carboxylate;

(5R,6S)-6-[(1R)-hydroxyethyl]-2-[4-(1-pyridinio)methylphenyl]sulfinylmethylpenem-3-carboxylate;

(5R,6S)-6-[(1R)-hydroxyethyl]-2-[4-(1-pyridinio)methylphenyl]sulfonylmethylpenem-3-carboxylate;

(5R,6S)-6-[(1R)-hydroxyethyl]-2-[4-(3,5-dimethyl-1-pyridinio)methylphenyl]oxymethylpenem-3-carboxylate;

(5R,6S)-6-[(1R)-hydroxyethyl]-2-[4-(3-hydroxy-1-pyridinio)methylphenyl]oxymethylpenem-3-carboxylate;

(5R,6S)-6-[(1R)-hydroxyethyl]-2-[4-(4-sulphoethyl-1-pyridinio)methylphenyl]oxymethylpenem-3-carboxylate;

(5R,6S)-6-[(1R)-hydroxyethyl]-2-[4-(3-hydroxymethyl-1-pyridinio)methylphenyl]oxymethylpenem-3-carboxylate;

(5R,6S)-6-[(1R)-hydroxyethyl]-2-[4-(2-hydroxyethyl-1-pyridinio)methylphenyl]oxymethylpenem-3-carboxylate;

(5R,6S)-6-[(1R)-hydroxyethyl]-2-[4-(8-hydroxy-1-quinolinio)methylphenyl]oxymethylpenem-3-carboxylate;

(5R,6S)-6-[(1R)-hydroxyethyl]-2-[4-(8-hydroxy-2-isoquinolinio)methylphenyl]oxymethylpenem-3-carboxylate;

(5R,6S)-6-[(1R)-hydroxyethyl]-2-[4-(3-formylamino-1-pyridinio)methylphenyl]oxymethylpenem-3-carboxylate;

(5R,6S)-6-[(1R)-hydroxyethyl]-2-[4-(4-hydroxyaminocarbonyl-1-pyridinio)methylphenyl]oxymethylpenem-3-carboxylate;

(5R,6S)-6-[(1R)-hydroxyethyl]-2-[4-(3-formyl-1-pyridinio)methylphenyl]oxymethylpenem-3-carboxylate;

(5R,6S)-6-[(1R)-hydroxyethyl]-2-[4-(3-hydroxyiminomethyl-1-pyridinio)methylphenyl]oxymethylpenem-3-carboxylate;

(5R,6S)-6-[(1R)-hydroxyethyl]-2-{4-[4-(1-hydroxyiminoethyl)-1-pyridinio]methylphenyl}oxymethylpenem-3-carboxylate;

(5R,6S)-6-[(1R)-hydroxyethyl]-2-[4-(3-amino-1-pyridinio)methylphenyl]oxymethylpenem-3-carboxylate;

(5R,6S)-6-[(1R)-hydroxyethyl]-2-[4-(1-pyrazinio)methylphenyl]oxymethylpenem-3-carboxylate;

(5R,6S)-6-[(1R)-hydroxyethyl]-2-[4-(1-methyl-1-triazolio)methylphenyl]oxymethylpenem-3-carboxylate;

(5R,6S)-6-[(1R)-hydroxyethyl]-2-[4-(2-methyl-1-pyrazolio)methylphenyl]oxymethylpenem-3-carboxylate;

(5R,6S)-6-[(1R)-hydroxyethyl]-2-[4-(thieno[2,3-c]pyridinio)methylphenyl]oxymethylpenem-3-carboxylate;

(5R,6S)-6-[(1R)-hydroxyethyl]-2-[4-(furo[2,3-c]pyridinio)methylphenyl]oxymethylpenem-3-carboxylate;

(5R,6S)-6-[(1R)-hydroxyethyl]-2-[4-(furo[3,2-c]pyridinio)methylphenyl]oxymethylpenem-3-carboxylate;

(5R,6S)-6-[(1R)-hydroxyethyl]-2-[4-(thieno[3,2-c]pyridinio)methylphenyl]oxymethylpenem-3-carboxylate;

(5R,6S)-6-[(1R)-hydroxyethyl]-2-[4-(thieno[2,3-b]pyridinio)methylphenyl]oxymethylpenem-3-carboxylate;

(5R,6S)-6-[(1R)-hydroxyethyl]-2-[4-(furo[2,3-b]pyridinio)methylphenyl]oxymethylpenem-3-carboxylate;

(5R,6S)-6-[(1R)-hydroxyethyl]-2-[4-(thieno[3,4-c]pyridinio)methylphenyl]oxymethylpenem-3-carboxylate;

(5R,6S)-6-[(1R)-hydroxyethyl]-2-[4-(thiazolo[4,5-c]pyridinio)methylphenyl]oxymethylpenem-3-carboxylate;

12. A pharmaceutical composition comprising an antibacterially effective amount of a compound of claim 1, or a pharmaceutically acceptable salt thereof in admixture with a pharmaceutically acceptable diluent or carrier.

13. The treatment of infectious diseases, said treatment comprising administering to a host in need of such treatment a therapeutically effective amount of a compound of claim 1 or of a pharmaceutically acceptable salt thereof.

* * * * *